United States Patent
Hamprecht et al.

(10) Patent No.: US 6,528,455 B1
(45) Date of Patent: Mar. 4, 2003

(54) PHENOXY-AND THIOPHENOXY ACRYLIC ACID COMPOUNDS AS HERBICIDES

(75) Inventors: Gerhard Hamprecht, Weinheim (DE); Michael Puhl, Lampertheim (DE); Robert Reinhard, Ludwigshafen (DE); Ingo Sagasser, Dannstadt-Schauernheim (DE); Cyrill Zagar, Ludwigshafen (DE); Karl-Otto Westphalen, Speyer (DE); Matthias Witschel, Bad Dürkheim (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/148,909

(22) PCT Filed: Dec. 15, 2000

(86) PCT No.: PCT/EP00/12799

§ 371 (c)(1), (2), (4) Date: Jun. 5, 2002

(87) PCT Pub. No.: WO01/44204

PCT Pub. Date: Jun. 21, 2001

(30) Foreign Application Priority Data

Dec. 16, 1999 (DE) .......................................... 199 60 811

(51) Int. Cl.$^7$ .................... C07D 239/54; C07D 239/56; C07D 251/38; C07D 209/45; A01N 43/38; A01N 43/54; A01N 43/64; C07C 205/37; C07C 217/84; C07C 265/12; C07C 331/28

(52) U.S. Cl. ...................... 504/129; 504/209; 504/227; 504/229; 504/236; 504/238; 504/239; 504/242; 504/130; 544/242; 544/298; 544/309; 544/215; 544/216; 544/219; 544/220; 548/543; 548/545

(58) Field of Search .................................. 504/129, 236, 504/239, 243, 242, 209, 238, 227, 229, 130; 544/242, 298, 309, 215, 216, 219, 220; 548/543, 545

(56) References Cited

U.S. PATENT DOCUMENTS 4,439,229 A * 3/1984 Swirhenbank ................. 71/96

FOREIGN PATENT DOCUMENTS

| EP | 584655 | * | 3/1994 |
| EP | 585964 | * | 3/1994 |
| EP | 796845 | * | 9/1997 |
| GB | 2163427 | * | 2/1986 |

* cited by examiner

Primary Examiner—Sabiha Qazi
(74) Attorney, Agent, or Firm—Keil & Weinkauf

(57) ABSTRACT

Phenoxy- and thiophenoxyacrylic acid compounds of the formula I

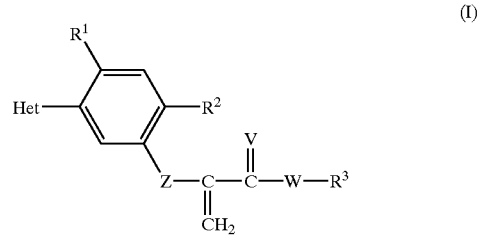

in which Het, $R^1$, $R^2$, $R^3$, V, W and Z are as defined in claim 1 and processes for their preparation, intermediates for their preparation, herbicidally active compositions comprising the compounds of the formula I and a method for controlling harmful fungi are described.

10 Claims, No Drawings

PHENOXY-AND THIOPHENOXY ACRYLIC ACID COMPOUNDS AS HERBICIDES

This application is a 371 of PCT/EP00/12799 filed on Dec. 15, 2000.

The present invention relates to 2-phenoxy- and 2-thiophenoxyacrylic acid compounds of the formula I

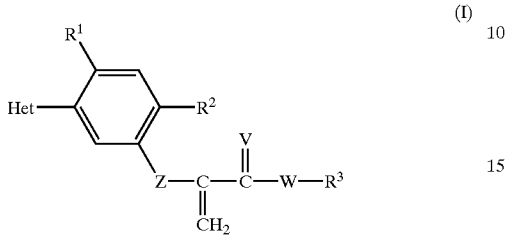

(I)

in which

Z, V and W independently of one another are oxygen or sulfur, $R^1$ is hydrogen or halogen and $R^2$ is halogen, cyano, $C_1$–$C_6$-alkyl, $C_1$–$C_6$-haloalkyl, $C_1$–$C_6$-alkoxy or $C_1$–$C_6$-haloalkoxy;

$R^3$ is hydrogen, $C_1$–$C_6$-alkyl, $C_2$–$C_6$-alkenyl, $C_3$–$C_6$-alkynyl, $C_1$–$C_6$-alkylamino-$C_1$–$C_6$-alkyl, ($C_1$–$C_6$-alkoxy)carbonyl-$C_1$–$C_6$-alkyl, $C_3$–$C_8$-cycloalkyl, 2,3-dihydrofuryl, 2,5-dihydrofuryl, tetrahydrofuryl, where each of the ten last mentioned groups may carry one, two or three substituents selected from the group consisting of:

halogen, nitro, cyano, hydroxyl, $C_3$–$C_6$-cycloalkyl, $C_1$–$C_6$-alkoxy, $C_1$–$C_6$-alkoxy-$C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkylcarbonyl, $C_1$–$C_6$-alkylcarbonyloxy, ($C_2$–$C_6$-alkenyl)carbonyloxy, ($C_2$–$C_6$-alkynyl)carbonyloxy, $C_1$–$C_6$-alkylthio, $C_1$–$C_6$-alkylsulfinyl, $C_1$–$C_6$-alkylsulfonyl, $C_1$–$C_6$-alkylideneiminooxy, =N—$OR^8$, —O—($C_nH_{2n-1}$) =N—$OR^8$ where n=1, 2, 3, 4, 5 or 6, phenyl, benzyloxy, phenoxy or phenylsulfonyl, where the three last mentioned groups may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy or $C_1$–$C_6$-alkoxycarbonyl;

is ($C_3$–$C_6$-alkenyloxy)carbonyl-$C_1$–$C_6$-alkyl, ($C_3$–$C_6$-alkynyloxy)carbonyl-$C_1$–$C_6$-alkyl, furyl or phenyl, where furyl and phenyl independently of one another may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy or $C_1$–$C_6$-alkoxycarbonyl;

Het is an unsaturated five- or six-membered heterocyclic radical which is attached to the phenyl ring of I via a nitrogen atom and which is selected from among radicals of the formulae II-1 to II-19:

(II-1)

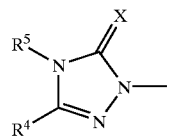

(II-2)

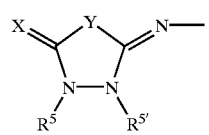

(II-3)

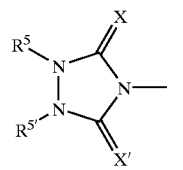

(II-4)

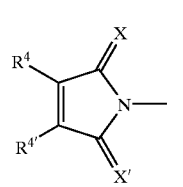

(II-5)

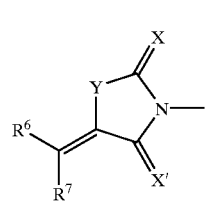

(II-6)

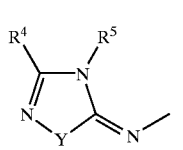

(II-7)

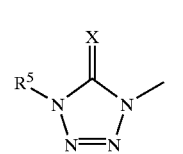

(II-8)

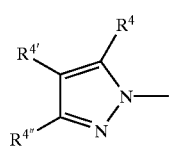

(II-9)

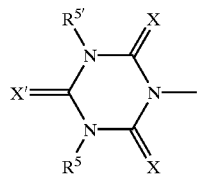

(II-10)

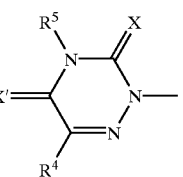

(II-11)

-continued

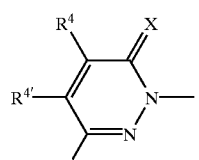 (II-12)

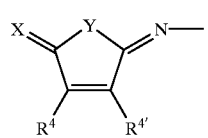 (II-13)

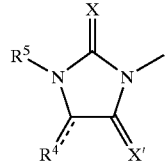 (II-14)

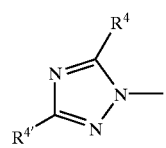 (II-15)

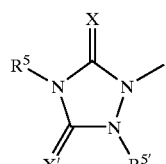 (II-16)

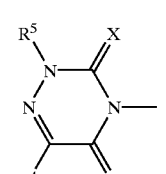 (II-17)

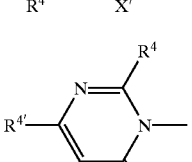 (II-18)

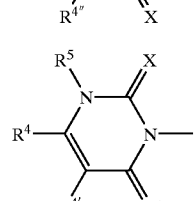 (II-19)

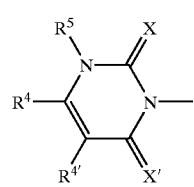

which === in the formula II-14 denotes a single bond or a double bond, $R^4$, $R^{4'}$ and $R^{4''}$ independently of one another are hydrogen, amino, $C_1$–$C_4$-alkylamino, di-$C_1$–$C_4$-alkylamino, saturated 5- or 6-membered N-bonded nitrogen heterocyclyl, $C_3$–$C_6$-cycloalkylamino, halogen, cyano, carboxyl, $C_1$–$C_6$-alkyl, $C_1$–$C_6$-haloalkyl, $C_3$–$C_6$-alkenyl, $C_3$–$C_6$-alkynyl, $C_1$–$C_6$-alkoxy, $C_1$–$C_6$-haloalkoxy, $C_1$–$C_6$-haloalkylthio, $C_1$–$C_6$-alkoxycarbonyl, $C_3$–$C_6$-alkenyloxy, $C_3$–$C_6$-alkynyloxy, $C_1$–$C_6$-alkylthio, $C_1$–$C_6$-alkylsulfinyl, $C_1$–$C_6$-alkylsulfonyl, $C_3$–$C_8$-cycloalkyl or $C_3$–$C_8$-cycloalkyl-$C_1$–$C_6$-alkyl, and $R^4$ in the formula II-14 also is a corresponding imino or alkylidene group if === denotes a double bond;

$R^5$ and $R^{5'}$ independently of one another are hydrogen, amino, hydroxyl, cyano, $C_1$–$C_6$-alkyl, $C_1$–$C_6$-haloalkyl, $C_3$–$C_6$-alkenyl, $C_3$–$C_6$-alkynyl, $C_1$–$C_6$-alkoxycarbonyl, $C_3$–$C_8$-cycloalkyl, $C_3$–$C_8$-cycloalkyl-$C_1$–$C_6$-alkyl, phenyl or phenyl-$C_1$–$C_6$-alkyl; and/or in each case two of the radicals $R^4$, $R^{4'}$, $R^{4''}$, $R^5$ and $R^{5'}$ together with the ring atoms of Het to which they are attached form a 4-, 5-, 6- or 7-membered ring which may be saturated or unsaturated, which may contain one or two nitrogen, oxygen and/or sulfur atoms as ring members and/or which may be substituted by one, two or three radicals selected from the group consisting of $C_1$–$C_4$-alkyl and halogen;

$R^6$ and $R^7$ independently of one another are hydrogen, $C_1$–$C_6$-alkyl, $C_1$–$C_6$-haloalkyl or $C_3$–$C_6$-cycloalkyl, or together with the C atom to which they are attached form a 4-, 5-, 6- or 7-membered ring which may be saturated or unsaturated, which may contain one or two oxygen and/or sulfur atoms as ring members and/or which may be substituted by one, two or three substituents selected from the group consisting of $C_1$–$C_4$-alkyl and halogen;

$R^8$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkyl)carbonyl-$C_1$–$C_6$-alkyl, ($C_1$–$C_6$-alkoxy)carbonyl-$C_1$–$C_6$-alkyl or ($C_1$–$C_6$-alkoxy)carbonyl-$C_2$–$C_6$-alkenyl;

Q in the formula II-1 is O or S,

X and X' independently of one another are O or S, and

Y is O, S or a group N—$R^9$ in which $R^9$ is hydrogen, $C_1$–$C_6$-alkyl, $C_1$–$C_6$-haloalkyl or $C_3$–$C_8$-cycloalkyl;

and the agriculturally useful salts of the compounds of the formula I.

Moreover, the invention relates to the use of the compounds I as herbicides, compositions which comprise the compounds I as herbicidally active substances, methods for controlling undesirable vegetation using the compounds of the formula I, and compounds of the formula III

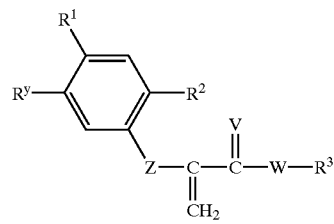 (III)

in which $R^1$, $R^2$, $R^3$, V, W and Z are as defined above and $R^y$ is —N=C=O, —N=C=S, —NH—NH$_2$, NO$_2$ or a group —NH—$R^{10}$ in which $R^{10}$ is hydrogen or $C_1$–$C_6$-alkylcarbonyl; and compounds of the formula IV

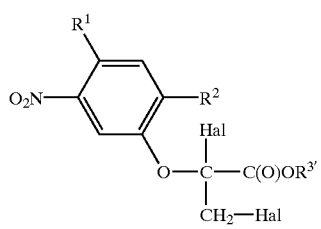

in which $R^1$ and $R^2$ are as defined above, Hal is a halogen atom, preferably chlorine or bromine, and $R^{3'}$ is selected from the group consisting of hydrogen, $C_1$–$C_6$-alkyl, $C_3$–$C_6$-cycloalkyl, ($C_1$–$C_6$-alkoxy) carbonyl-$C_1$–$C_6$-alkyl and phenyl which may carry one, two or three substituents selected from the group consisting of halogen, cyano, $C_1$–$C_6$-alkyl, $C_1$–$C_5$-haloalkyl, $C_1$–$C_6$-alkoxy, $C_1$–$C_6$-haloalkoxy and $C_1$–$C_6$-alkoxycarbonyl, and $R^3$ is preferably hydrogen, $C_1$–$C_6$-alkyl, $C_1$–$C_6$-haloalkyl or $C_1$–$C_6$-cyanoalkyl, the compounds of the formulae III and IV serving as intermediates for the preparation of the compounds I.

EP-A 255 047 discloses phenyluracils which have, at the phenyl ring, in the m-position to the uracil group, an ether group, a (thio)carbonyl group, which is attached via an oxygen atom, or a sulfonyloxy group.

EP-A 83 055 discloses N-(2-fluorophenyl) tetrahydrophthalimides which, in the 5-position of the phenyl ring, have a group which is attached via an oxygen atom or a nitrogen atom and which is derived from an α-amino- or α-hydroxycarboxylic acid.

It is an object of the present invention to provide novel herbicidally active compounds which allow better targeted control of undesirable plants than the known active compounds.

We have found that this object is achieved by the phenoxy- and phenylthioacrylic acid compounds of the formula I defined at the outset which, at the phenyl ring, have a 5- or 6-membered heterocycle Het of the formulae II-1 to II-19 defined at the outset which is attached via a nitrogen atom.

Furthermore, we have found herbicidal compositions which comprise the compounds I and have very good herbicidal activity. Moreover, we have found processes for preparing these compositions and methods for controlling undesirable vegetation using the compounds I.

The compounds of the formula I can contain one or more chiral centers in the substituents, in which case they are present as enantiomer or diastereomer mixtures. The invention provides both the pure enantiomers or diastereomers and mixtures thereof.

Agriculturally useful salts are especially the salts of those cations or the acid addition salts of those acids whose cations and anions, respectively, have no adverse effect on the herbicidal activity of the compounds I. Thus, particularly suitable cations are the ions of the alkali metals, preferably sodium and potassium, of the alkaline earth metals, preferably calcium, magnesium and barium, and of the transition metals, preferably manganese, copper, zinc and iron, and also the ammonium ion which may, if desired, carry one to four $C_1$–$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and also the anions of $C_1$–$C_4$-alkanoic acids, preferably formate, acetate, propionate and butyrate. They can be formed by reacting I with an acid of the corresponding anion, preferably hydrochloric acid, hydrobromic acid, sulfuric acid, phosphoric acid or nitric acid.

The organic molecular moieties mentioned in the definition of the substituents $R^1$ to $R^{10}$ or as radicals on cycloalkyl, phenyl or heterocyclic rings are—like the term halogen—collective terms for individual listings of the individual group members. All carbon chains, i.e. all alkyl, haloalkyl, cyanoalkyl, hydroxyalkyl, aminoalkyl, hydroxycarbonylalkyl, phenylalkyl, alkoxy, haloalkoxy, alkylthio, alkylsulfinyl, alkylsulfonyl, alkenyl, haloalkenyl, alkenyloxy, alkynyl, haloalkynyl, alkynyloxy, alkylideneimino and alkyloxyimino moieties, can be straight-chain or branched. Halogenated substituents preferably carry one, two, three, four or five identical or different halogen atoms. The term halogen represents in each case fluorine, chlorine, bromine or iodine, preferably fluorine or chlorine. $C_1$–$C_n$ is the possible number of carbon atoms in the hydrocarbon chain of the substituents or substituent moieties in question.

Examples of other meanings are:

$C_1$–$C_4$-alkyl: $CH_3$, $C_2H_5$, n-propyl, $CH(CH_3)_2$, n-butyl, $CH(CH_3)$—$C_2H_5$, 2-methylpropyl or $C(CH_3)_3$, in particular $CH_3$, $C_2H_5$ or $CH(CH_3)_2$;

$C_1$–$C_4$-haloalkyl: a $C_1$–$C_4$-alkyl radical as mentioned above which is partially or fully substituted by fluorine, chlorine, bromine and/or iodine, i.e., for example, $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular $CH_2F$, $CHF_2$, $CF_3$, $CH_2Cl$, 2-fluoroethyl, 2-chloroethyl or 2,2,2-trifluoroethyl;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $CH_3$, $C_2H_5$, n-propyl, $CH(CH_3)_2$, n-butyl, $C(CH_3)_3$, n-pentyl or n-hexyl;

$C_1$–$C_6$-haloalkyl: $C_1$–$C_6$-alkyl as mentioned above which is partially or fully substituted by fluorine, chlorine, bromine and/or iodine, for example one of the radicals mentioned under $C_1$–$C_4$-haloalkyl, and 5-fluoro-1- pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

$C_1$–$C_4$-alkoxy: $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $C(CH_3)_3$, preferably $OCH_3$, $OC_2H_5$ or $OCH(CH_3)_2$;

$C_1$–$C_6$-alkoxy: a $C_1$–$C_4$-alkoxy radical as mentioned above and, for example, n-pentoxy, 1-methylbutoxy, 2-methylbutoxy, 3-methylbutoxy, 2,2-dimethylpropoxy, 1-ethylpropoxy, n-hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably $OCH_3$, $OC_2H_5$, $OCH_2$—$C_2H_5$, $OCH(CH_3)_2$, n-butoxy, $OC(CH_3)_3$, n-pentoxy or n-hexoxy;

$C_1$–$C_4$-haloalkoxy: a $C_1$–$C_4$-alkoxy radical as mentioned above which is partially or fully substituted by fluorine, chlorine, bromine and/or iodine, i.e., for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, in particular 2-chloroethoxy or 2,2,2-trifluoroethoxy;

$C_1$–$C_6$-haloalkoxy: a $C_1$–$C_6$-alkoxy radical as mentioned above which is partially or fully substituted by fluorine, chlorine, bromine and/or iodine, i.e., for example, one of the radicals mentioned under $C_1$–$C_4$-haloalkoxy, and 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy;

($C_1$–$C_6$-alkyl)carbonyl: a $C_1$–$C_6$-alkyl group which is attached via a carbonyl group, for example: CO—$CH_3$, CO—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular CO—$CH_3$, CO—$C_2H_5$ or CO—$CH(CH_3)_2$;

($C_1$–$C_6$-alkyl)carbonyl-$C_1$–$C_6$-alkyl: $C_1$–$C_6$-alkyl which is substituted by ($C_1$–$C_6$-alkyl)carbonyl as mentioned above, i.e., for example, methylcarbonylmethyl;

($C_1$–$C_6$-alkoxy)carbonyl: a $C_1$–$C_6$-alkoxy group which is attached via a carbonyl group, for example: CO—$OCH_3$, CO—$OC_2H_5$, COO—$CH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$, CO—$OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-diethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular CO—$OCH_3$, CO—$OC_2H_5$, CO—$OCH(CH_3)_2$ or CO—$OCH_2$—$CH(CH_3)_2$;

($C_1$–$C_6$-alkoxy)carbonyl-$C_1$–$C_6$-alkyl: $C_1$–$C_6$-alkyl, preferably $C_1$–$C_4$-alkyl, which is substituted by ($C_1$–$C_6$-alkoxy)carbonyl, in particular by ($C_1$–$C_4$-alkoxy)carbonyl—as mentioned above—, for example, $CH_2$—CO—$OCH_3$, $CH_2$—CO—$OC_2H_5$, $CH_2$—CO—$OCH_2$—$C_2H_5$, $CH_2$—CO—$OCH(CH_3)_2$, n-butoxycarbonylmethyl, $CH_2$—CO—$OCH(CH_3)$—$C_2H_5$, $CH_2$—CO—$OCH_2$—$CH(CH_3)_2$, $CH_2$—CO—$OC(CH_3)_3$, 1-(CO—$OCH_3$)-ethyl, 1-(CO—$OC_2H_5$)-ethyl, 1-(CO—$OCH_2$—$C_2H_5$)-ethyl, 1-[$CH(CH_3)_2$]-ethyl, 1-(n-butoxycarbonyl)-ethyl, 1-[1-methylpropoxycarbonyl]-ethyl, 1-[2-methylpropoxycarbonyl]-ethyl, 2-(CO—$OCH_3$)-ethyl, 2-(CO—$OC_2H_5$)-ethyl, 2-(CO—$OCH_2$—$C_2H_5$)-ethyl, 2-[CO—$OCH(CH_3)_2$]-ethyl, 2-(n-butoxycarbonyl)-ethyl, 2-[1-methylpropoxycarbonyl]-ethyl, 2-[2-methylpropoxycarbonyl]-ethyl, 2-[CO—$OC(CH_3)_3$]-ethyl, 2-(CO—$OCH_3$)-propyl, 2-(CO—$OC_2H_5$)-propyl, 2-(CO—$OCH_2$—$C_2H_5$)-propyl, 2-[CO—$OCH(CH_3)_2$]-propyl, 2-(n-butoxycarbonyl)-propyl, 2-[1-methylpropoxycarbonyl]-propyl, 2-[2-methylpropoxycarbonyl]-propyl, 2-[CO—$OC(CH_3)_3$]-propyl, 3-(CO—$OCH_3$)-propyl, 3-(CO—$OC_2H_5$)-propyl, 3-(CO—$OCH_2$—$C_2H_5$)-propyl, 3-[CO—$OCH(CH_3)_2$]-propyl, 3-(n-butoxycarbonyl)propyl, 3-[1-methylpropoxycarbonyl]-propyl, 3-[2- methylpropoxycarbonyl]-propyl, 3-[CO—OC(CH$_3$)$_3$]-propyl, 2-(CO—OCH$_3$)-butyl, 2-(CO—OC$_2$H$_5$)-butyl, 2-(CO—OCH$_2$—C$_2$H$_5$)-butyl, 2-[CO—OCH(CH$_3$)$_2$]-butyl, 2-(n-butoxycarbonyl)-butyl, 2-[1-methylpropoxycarbonyl]-butyl, 2-[2-methylpropoxycarbonyl]-butyl, 2-[CO—OC(CH$_3$)$_3$]-butyl, 3-(CO—OCH$_3$)-butyl, 3-(CO—OC$_2$H$_5$)-butyl, 3-(CO—OCH$_2$—C$_2$H$_5$)-butyl, 3-[COOCH(CH$_3$)$_2$]-butyl, 3-(n-butoxycarbonyl)-butyl, 3-[1-methylpropoxycarbonyl]-butyl, 3-[2-methylpropoxycarbonyl]-butyl, 3-[C—OC(CH$_3$)$_3$]-butyl, 4-(CO—OCH$_3$)-butyl, 4-(CO—OC$_2$H$_5$)-butyl, 4-(CO—OCH$_2$—C$_2$H$_5$)-butyl, 4-[COOCH(CH$_3$)$_2$]-butyl, 4-(n-butoxycarbonyl)-butyl, 4-[1-methylpropoxycarbonyl]-butyl, 4-[2-methylpropoxycarbonyl]-butyl or 4-[CO—OC(CH$_3$)$_3$]-butyl, preferably CH$_2$—CO—OCH$_3$, CH$_2$—CO—OC$_2$H$_5$, 1-(CO—OCH$_3$)-ethyl or 1-(CO—OC$_2$H$_5$)-ethyl;

C$_1$–C$_6$-alkylamino-C$_1$–C$_6$-alkyl: C$_1$–C$_6$-alkyl which is substituted by a C$_1$–C$_6$-alkylamino group, for example CH$_2$—NH—CH$_3$, CH$_2$—NH—C$_2$H$_5$, CH$_2$—NH—CH$_2$—C$_2$H$_5$, CH$_2$—NH—CH(CH$_3$)$_2$, CH$_2$—NH—(CH$_2$)$_3$—CH$_3$, CH$_2$—NH—CH(CH$_3$)—C$_2$H$_5$, CH$_2$—NH—CH$_2$—CH(CH$_3$)$_2$, CH$_2$—NH—C(CH$_3$)$_3$, CH$_2$—NH—(CH$_2$)$_4$—CH$_3$, (1-methylbutylamino)methyl, (2-methylbutylamino)methyl, (3-methylbutylamino)methyl, (2,2-dimethylpropylamino)methyl, (1-ethylpropylamino)methyl, n-hexylaminomethyl, (1,1-dimethylpropylamino)methyl, (1,2-dimethylpropylamino)methyl, (1-methylpentylamino)methyl, (2-methylpentylamino)methyl, (3-methylpentylamino)methyl, (4-methylpentylamino)methyl, (1,1-dimethylbutylamino)methyl, (1,2-dimethylbutylamino)methyl, (1,3-dimethylbutylamino)methyl, (2,2-dimethylbutylamino)methyl, (2,3-dimethylbutylamino)methyl, (3,3-dimethylbutylamino)methyl, (1-ethylbutylamino)methyl, (2-ethylbutylamino)methyl, (1,1,2-trimethylpropylamino)methyl, (1,2,2-trimethylpropylamino)methyl, (1-ethyl-1-methylpropylamino)methyl, (1-ethyl-2-methylpropylamino)methyl, methylaminoethyl, ethylaminoethyl, n-propylaminoethyl, (1-methylethylamino)ethyl, n-butylaminoethyl, (1-methylpropylamino)ethyl, (2-methylpropylamino)ethyl, (1,1-dimethylethylamino)ethyl, n-pentylaminoethyl, (1-methylbutylamino)ethyl, (2-methylbutylamino)ethyl, (3-methylbutylamino)ethyl, (2,2-dimethylpropylamino)ethyl, (1-ethylpropylamino)ethyl, n-hexylaminoethyl, (1,1-dimethylpropylamino)ethyl, (1,2-dimethylpropylamino)ethyl, (1-methylpentylamino)ethyl, (2-methylpentylamino)ethyl, (3-methylpentylamino)ethyl, (4-methylpentylamino)ethyl, (1,1-dimethylbutylamino)ethyl, (1,2-dimethylbutylamino)ethyl, (1,3-dimethylbutylamino)ethyl, (2,2-dimethylbutylamino)ethyl, (2,3-dimethylbutylamino)ethyl, (3,3-dimethylbutylamino)ethyl, (1-ethylbutylamino)ethyl, (2-ethylbutylamino)ethyl, (1,1,2-trimethylpropylamino)ethyl, (1,2,2-trimethylpropylamino)ethyl, (1-ethyl-1-methylpropylamino)ethyl, (1-ethyl-2-methylpropylamino)ethyl, 2-(methylamino)propyl, 3-(methylamino)propyl and 2-(ethylamino)propyl, preferably C$_1$–C$_6$-alkylaminomethyl and C$_1$–C$_6$-alkylaminoethyl;

C$_1$–C$_6$-alkylthio: SCH$_3$, SC$_2$H$_5$, SCH$_2$—C$_2$H$_5$, SCH(CH$_3$)$_2$, n-butylthio, 1-methylpropylthio, 2-methylpropylthio, SC(CH$_3$)$_3$, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, in particular SCH$_3$ or SC$_2$H$_5$;

C$_1$–C$_6$-alkylthio-C$_1$–C$_6$-alkyl: C$_1$–C$_6$-alkyl which is substituted by C$_1$–C$_6$-alkylthio—as mentioned above—, i.e., for example, CH$_2$—SCH$_3$, CH$_2$—SC$_2$H$_5$, n-propylthiomethyl, CH$_2$—SCH(CH$_3$)$_2$, n-butylthiomethyl, (1-methylpropylthio)methyl, (2-methylpropylthio)methyl, CH$_2$—SC(CH$_3$)$_3$, 2-(methylthio)ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl or 4-(1,1-dimethylethylthio)butyl, preferably CH$_2$—SCH$_3$, CH$_2$—SC$_2$H$_5$, 2-(SCH$_3$)-ethyl or 2-(SC$_2$H$_5$)-ethyl;

C$_1$–C$_4$-haloalkylthio: a C$_1$–C$_4$-alkylthio radical as mentioned above which is partially or fully substituted by fluorine, chlorine, bromine and/or iodine, i.e., for example, SCH$_2$F, SCHF$_2$, SCF$_3$, SCH$_2$Cl, SCH(Cl)$_2$, SC(Cl)$_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, SC$_2$F$_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, SCH$_2$—C$_2$F$_5$, SCF$_2$—C$_2$F$_5$, 1-(CH$_2$F)-2-fluoroethylthio, 1-(CH$_2$Cl)-2-chloroethylthio, 1-(CH$_2$Br)-2- bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

$C_1$–$C_6$-alkylsulfinyl: SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular SO—$CH_3$;

$C_1$–$C_6$-alkylsulfinyl-$C_1$–$C_6$-alkyl: $C_1$–$C_6$-alkyl which is substituted by $C_1$–$C_6$-alkylsulfinyl, for example methylsulfinylethyl, ethylsulfinylethyl, methylsulfinylpropyl, ethylsulfinylpropyl;

$C_1$–$C_6$-alkylsulfonyl: $SO_2$—$CH_3$, $SO_2$—$C_2H_5$, n-propylsulfonyl, $SO_2$—$CH(CH_3)_2$, n-butylsulfonyl, 1-methylpropylsulfonyl, 2-methylpropylsulfonyl, $SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular $SO_2$—$CH_3$;

$C_1$–$C_6$-alkylsulfonyl-$C_1$–$C_6$-alkyl: $C_1$–$C_6$-alkyl which is substituted by $C_1$–$C_6$-alkylsulfonyl, for example methylsulfonylethyl, ethylsulfonylethyl, methylsulfonylpropyl, ethylsulfonylpropyl;

$C_1$–$C_6$-alkylideneiminooxy: for example methylideneiminooxy, ethylideneiminooxy, 1-propylideneiminooxy, 2-propylideneiminooxy, 1-butylideneiminooxy, 2-butylideneiminooxy or 2-hexylideneiminooxy;

$C_1$–$C_6$-alkylideneiminooxy-$C_1$–$C_6$-alkyl: $C_1$–$C_6$-alkyl which is substituted by $C_1$–$C_6$-alkylideneiminooxy, for example methylideneiminooxymethyl, ethylideneiminooxymethyl, propylideneiminooxymethyl, methylideneiminooxyethyl, ethylideneiminooxyethyl, propylideneiminooxyethyl, methylideneiminooxypropyl, ethylideneiminooxypropyl, propylideneiminooxypropyl;

$C_1$-$C_6$-alkoxy-$C_1$–$C_6$-alkylamino-$C_1$–$C_6$-alkyl: $C_1$–$C_6$-alkylamino-$C_1$–$C_6$-alkyl which is substituted in the alkylamino moiety by $C_1$–$C_6$-alkoxy—as mentioned above—i.e., for example, $CH_2$—NH—$CH_2$—$OCH_3$ or $CH_2$—NH—$CH_2$—$OC_2H_5$; $C_1$–$C_6$-alk(yl)oxyimino: a group R—O—N= in which R is $C_1$–$C_6$-alkyl, for example methoxyimino, ethoxyimino, 1-propoxyimino, 2-propoxyimino, 1-methylethoxyimino, n-butoxyimino, sec-butoxyimino, tert-butoxyimino, 1-methyl-1-propoxyimino, 2-methyl-1-propoxyimino, 1-methyl-2-propoxyimino, 2-methyl-2-propoxyimino, n-pentoxyimino, 2-pentoxyimino, 3-pentoxyimino, 4-pentoxyimino, 1-methyl-1-butoxyimino, 2-methyl-1-butoxyimino, 3-methyl-1-butoxyimino, 1-methyl-2-butoxyimino, 2-methyl-2-butoxyimino, 3-methyl-2-butoxyimino, 1-methyl-3-butoxyimino, 2-methyl-3-butoxyimino, 3-methyl-3-butoxyimino, 1,1-dimethyl-2-propoxyimino, 1,2-dimethyl-1-propoxyimino, 1,2-dimethyl-2-propoxyimino, 1-ethyl-1-propoxyimino, 1-ethyl-2-propoxyimino, n-hexoxyimino, 2-hexoxyimino, 3-hexoxyimino, 4-hexoxyimino, 5-hexoxyimino, 1-methyl-1-pentoxyimino, 2-methyl-1-pentoxyimino, 3-methyl-1-pentoxyimino, 4-methyl-1-pentoxyimino, 1-methyl-2-pentoxyimino, 2-methyl-2-pentoxyimino, 3-methyl-2-pentoxyimino, 4-methyl-2-pentoxyimino, 1-methyl-3-pentoxyimino, 2-methyl-3-pentoxyimino, 3-methyl-3-pentoxyimino, 4-methyl-3-pentoxyimino, 1-methyl-4-pentoxyimino, 2-methyl-4-pentoxyimino, 3-methyl-4-pentoxyimino, 4-methyl-4-pentoxyimino, 1,1-dimethyl-2-butoxyimino, 1,1-dimethyl-3-butoxyimino, 1,2-dimethyl-1-butoxyimino, 1,2-dimethyl-2-butoxyimino, 1,2-dimethyl-3-butoxyimino, 1,3-dimethyl-1-butoxyimino, 1,3-dimethyl-2-butoxyimino, 1,3-dimethyl-3-butoxyimino, 2,2-dimethyl-3-butoxyimino, 2,3-dimethyl-1-butoxyimino, 2,3-dimethyl-2-butoxyimino, 2,3-dimethyl-3-butoxyimino, 3,3-dimethyl-1-butoxyimino, 3,3-dimethyl-2-butoxyimino, 1-ethyl-1-butoxyimino, 1-ethyl-2-butoxyimino, 1-ethyl-3-butoxyimino, 2-ethyl-1-butoxyimino, 2-ethyl-2-butoxyimino, 2-ethyl-3-butoxyimino, 1,1,2-trimethyl-2-propoxyimino, 1-ethyl-1-methyl-2-propoxyimino, 1-ethyl-2-methyl-1-propoxyimino and 1-ethyl-2-methyl-2-propoxyimino;

$C_1$–$C_6$-alkoxy-$C_1$–$C_6$-alkyl: $C_1$–$C_6$-alkyl which is substituted by $C_1$–$C_6$-alkoxy—as mentioned above—, i.e., for example, $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy) butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular $CH_2$—$OCH_3$ or 2-methoxyethyl;

$C_1$–$C_6$-alkoxyimino-$C_1$–$C_6$-alkyl: $C_1$–$C_6$-alkyl which is substituted by a $C_1$–$C_6$-alkyloxyimino group as defined above, for example methoxyiminomethyl, ethoxyiminomethyl, methoxyiminoethyl, ethoxyiminoethyl, methoxyiminopropyl, propyloxyiminopropyl;

$C_1$–$C_6$-alkoxyimino-$C_1$–$C_6$-alkoxy-$C_1$–$C_6$-alkyl: $C_1$–$C_6$-alkoxy-$C_1$–$C_6$-alkyl which is substituted in the alkoxy moiety by a $C_1$–$C_6$-alkyloxyimino group as defined above, for example methoxyiminoethoxymethyl, ethoxyiminoethoxymethyl, methoxyiminoethoxyethyl, ethoxyiminoethoxyethyl, methoxyiminoethoxypropyl, propyloxyiminoethoxypropyl;

$C_1$–$C_6$-alkoxy-$C_1$–$C_6$-alkoxy: $C_1$–$C_6$-alkoxy which is substituted by $C_1$–$C_6$-alkoxy—as mentioned above—, for example $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $CH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(n-propoxy)butoxy, 3-(1-methylethoxy)butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-methylethoxy)butoxy, 4-(n-butoxy)butoxy, 4-(1-methylpropoxy)butoxy, 4-(2-methylpropoxy)butoxy or 4-(1,1-dimethylethoxy)butoxy, in particular $OCH_2$—$OCH_3$ or 2-methoxyethoxy;

$C_1$–$C_6$-alkoxy-$C_1$–$C_6$-alkoxy-$C_1$–$C_6$-alkyl: $C_1$–$C_6$-alkyl which is substituted by $C_1$–$C_6$-alkoxy-$C_1$–$C_6$-alkoxy—as mentioned above—, for example methoxyethoxyethyl, ethoxyethoxyethyl;

$C_3$–$C_6$-alkenyl: for example prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-2-en-1-yl, 2,3-dimethylbut-2-en-1-yl, 2,3-dimethylbut-3-en-1-yl, 3,3-dimethylbut-2-en-1-yl, 2,2-dimethylbut-3-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular prop-2-en-1-yl or n-buten-4-yl;

$C_2$–$C_6$-alkenyl: ethenyl or one of the radicals mentioned under $C_3$–$C_6$-alkenyl, in particular ethenyl or prop-2-en-1-yl;

$C_3$–$C_6$-haloalkenyl: $C_3$–$C_6$-alkenyl as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkenyloxy: prop-1-en-1-yloxy, prop-2-en-1-yloxy, n-but-1-en-1-yloxy, n-but-1-en-3-yloxy, n-but-1-en-4-yloxy, n-but-2-en-1-yloxy, n-pent-1-en-1-yloxy, n-pent-1-en-3-yloxy, n-pent-1-en-4-yloxy, n-pent-1-en-5-yloxy, n-pent-2-en-1-yloxy, n-pent-2-en-4-yloxy, n-pent-2-en-5-yloxy, 3-methylbut-1-en-3-yloxy, 3-methylbut-1-en-4-yloxy, n-hex-1-en-1-yloxy, n-hex-1-en-3-yloxy, n-hex-1-en-4-yloxy, n-hex-1-en-5-yloxy, n-hex-1-en-6-yloxy, n-hex-2-en-1-yloxy, n-hex-2-en-4-yloxy, n-hex-2-en-5-yloxy, n-hex-2-en-6-yloxy, n-hex-3-en-1-yl-oxy, n-hex-3-en-2-yloxy, 3-methylpent-1-en-1-yloxy, 3-methylpent-1-en-3-yloxy, 3-methylpent-1-en-4-yloxy, 3-methylpent-1-en-5-yloxy, 4-methylpent-1-en-1-yloxy, 4-methylpent-2-en-4-yloxy or 4-methylpent-2-en-5-yloxy, in particular prop-2-en-1-yloxy;

$C_3$–$C_6$-alkenyloxy-$C_1$–$C_6$-alkyl: $C_1$–$C_6$-alkyl which is substituted by $C_3$–$C_4$-alkenyloxy such as allyloxy, but-1-en-3-yloxy, but-1-en-4-yloxy, but-2-en-1-yloxy, 1-methylprop-2-enyloxy or 2-methylprop-2-enyloxy, i.e., for example, allyloxymethyl, 2-allyloxyethyl or but-1-en-4-yloxymethyl, in particular 2-allyloxyethyl;

$C_3$–$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular prop-2-yn-1-yl;

$C_2$–$C_6$-alkynyl: ethynyl or one of the radicals mentioned under $C_3$–$C_6$-alkynyl, in particular ethynyl or prop-2-yn-1-yl; $C_3$–$C_6$-haloalkynyl: $C_3$–$C_6$-alkynyl as mentioned above which is partially or fully substituted by fluorine, chlorine, bromine and/or iodine, i.e., for example, 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluorohex-4-yn-1-yl;

$C_3$–$C_6$-alkynyloxy: prop-1-yn-1-yloxy, prop-2-yn-1-yloxy, n-but-1-yn-1-yloxy, n-but-1-yn-3-yloxy, n-but- 1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular prop-2-yn-1-yloxy;

$C_2$–$C_6$-alkynyloxy: ethynyloxy or one of the radicals mentioned under $C_3$–$C_6$-alkynyloxy, in particular ethynyloxy or prop-2-yn-1-yloxy;

$C_3$–$C_6$-alkynyloxy-$C_1$–$C_6$-alkyl: $C_1$–$C_6$-alkyl which is substituted by $C_3$–$C_6$-alkynyloxy such as propargyloxy, but-1-yn-3-yloxy, but-1-yn-4-yloxy, but-2-yn-1-yloxy, 1-methylprop-2-ynyloxy or 2-methylprop-2-ynyloxy, preferably by propargyloxy, i.e., for example, propargyloxymethyl or 2-propargyloxyethyl, in particular 2-propargyloxyethyl;

($C_3$–$C_6$-alkenyloxy)carbonyl: prop-1-en-1-yloxycarbonyl, prop-2-en-1-yloxycarbonyl, 1-methylethenyloxycarbonyl, n-buten-1-yloxycarbonyl, n-buten-2-yloxycarbonyl, n-buten-3-yloxycarbonyl, 1-methylprop-1-en-1-yloxycarbonyl, 2-methylprop-1-en-1-yloxycarbonyl, 1-methylprop-2-en-1-yloxycarbonyl, 2-methylprop-2-en-1-yloxycarbonyl, n-penten-1-yloxycarbonyl, n-penten-2-yloxycarbonyl, n-penten-3-yloxycarbonyl, n-penten-4-yloxycarbonyl, 1-methylbut-1-en-1-yloxycarbonyl, 2-methylbut-1-en-1-yloxycarbonyl, 3-methylbut-1-en-1-yloxycarbonyl, 1-methylbut-2-en-1-yloxycarbonyl, 2-methylbut-2-en-1-yloxycarbonyl, 3-methylbut-2-en-1-yloxycarbonyl, 1-methylbut-3-en-1-yloxycarbonyl, 2-methylbut-3-en-1-yloxycarbonyl, 3-methylbut-3-en-1-yloxycarbonyl, 1,1-dimethylprop-2-en-1-yloxycarbonyl, 1,2-dimethylprop-1-en-1-yloxycarbonyl, 1,2-dimethylprop-2-en-1-yloxycarbonyl, 1-ethylprop-1-en-2-yloxycarbonyl, 1-ethylprop-2-en-1-yloxycarbonyl, n-hex-1-en-1-yloxycarbonyl, n-hex-2-en-1-yloxycarbonyl, n-hex-3-en-1-yloxycarbonyl, n-hex-4-en-1-yloxycarbonyl, n-hex-5-en-1-yloxycarbonyl, 1-methylpent-1-en-1-yloxycarbonyl, 2-methylpent-1-en-1-yloxycarbonyl, 3-methylpent-1-en-1-yloxycarbonyl, 4-methylpent-1-en-1-yloxycarbonyl, 1-methylpent-2-en-1-yloxycarbonyl, 2-methylpent-2-en-1-yloxycarbonyl, 3-methylpent-2-en-1-yloxycarbonyl, 4-methylpent-2-en-1-yloxycarbonyl, 1-methylpent-3-en-1-yloxycarbonyl, 2-methylpent-3-en-1-yloxycarbonyl, 3-methylpent-3-en-1-yloxycarbonyl, 4-methylpent-3-en-1-yloxycarbonyl, 1-methylpent-4-en-1-yloxycarbonyl, 2-methylpent-4-en-1-yloxycarbonyl, 3-methylpent-4-en-1-yloxycarbonyl, 4-methylpent-4-en-1-yloxycarbonyl, 1,1-dimethylbut-2-en-1-yloxycarbonyl, 1,1-dimethylbut-3-en-1-yloxycarbonyl, 1,2-dimethylbut-1-en-1-yloxycarbonyl, 1,2-dimethylbut-2-en-1-yloxycarbonyl, 1,2-dimethylbut-3-en-1-yloxycarbonyl, 1,3-dimethylbut-1-en-1-yloxycarbonyl, 1,3-dimethylbut-2-en-1-yloxycarbonyl, 1,3-dimethylbut-3-en-1-yloxycarbonyl, 2,2-dimethylbut-3-en-1-yloxycarbonyl, 2,3-dimethylbut-1-en-1-yloxycarbonyl, 2,3-dimethylbut-2-en-1-yloxycarbonyl, 2,3-dimethylbut-3-en-1-yloxycarbonyl, 3,3-dimethylbut-1-en-1-yloxycarbonyl, 3,3-dimethylbut-2-en-1-yloxycarbonyl, 1-ethylbut-1-en-1-yloxycarbonyl, 1-ethylbut-2-en-1-yloxycarbonyl, 1-ethylbut-3-en-1-yloxycarbonyl, 2-ethylbut-1-en-1-yloxycarbonyl, 2-ethylbut-2-en-1-yloxycarbonyl, 2-ethylbut-3-en-1-yloxycarbonyl, 1,1,2-trimethylprop-2-en-1-yloxycarbonyl, 1-ethyl-1-methylprop-2-en-1-yloxycarbonyl, 1-ethyl-2-methylprop-1-en-1-yloxycarbonyl or 1-ethyl-2-methylprop-2-en-1-yloxycarbonyl, in particular prop-2-en-1-yloxycarbonyl;

($C_3$–$C_6$-alkenyloxy)carbonyl-$C_1$–$C_6$-alkyl: $C_1$–$C_6$-alkyl which is substituted by ($C_3$–$C_6$-alkenyloxy)carbonyl, as mentioned above, preferably by prop-2-en-1-yloxycarbonyl, i.e., for example, prop-2-en-1-yloxycarbonylmethyl, 2-(prop-2-en-1-yloxycarbonyl) propyl;

($C_2$–$C_6$-alkenyl)carbonyloxy: ethenylcarbonyloxy, prop-1-en-1-ylcarbonyloxy, prop-2-en-1-ylcarbonyloxy, 1-methylethenylcarbonyloxy, n-buten-1-ylcarbonyloxy, n-buten-2-ylcarbonyloxy, n-buten-3-ylcarbonyloxy, 1-methylprop-1-en-1-ylcarbonyloxy, 2-methylprop-1-en-1-ylcarbonyloxy, 1-methylprop-2-en-1-ylcarbonyloxy, 2-methylprop-2-en-1-ylcarbonyloxy, n-penten-1-ylcarbonyloxy, n-penten-2-ylcarbonyloxy, n-penten-3-ylcarbonyloxy, n-penten-4-ylcarbonyloxy, 1-methylbut-1-en-1-ylcarbonyloxy, 2-methylbut-1-en-1-ylcarbonyloxy, 3-methylbut-1-en-1-ylcarbonyloxy, 1-methylbut-2-en-1-ylcarbonyloxy, 2-methylbut-2-en-1-ylcarbonyloxy, 3-methylbut-2-en-1-ylcarbonyloxy, 1-methylbut-3-en-1-ylcarbonyloxy, 2-methylbut-3-en-1-ylcarbonyloxy, 3-methylbut-3-en-1-ylcarbonyloxy, 1,1-dimethylprop-2-en-1-ylcarbonyloxy, 1,2-dimethylprop-1-en-1-ylcarbonyloxy, 1,2-dimethylprop-2-en-1-ylcarbonyloxy, 1-ethylprop-1-en-2-ylcarbonyloxy, 1-ethylprop-2-en-1-ylcarbonyloxy, n-hex-1-en-1-ylcarbonyloxy, n-hex-2-en-1-ylcarbonyloxy, n-hex-3-en-1-ylcarbonyloxy, n-hex-4-en-1-ylcarbonyloxy, n-hex-5-en-1-ylcarbonyloxy, 1-methylpent-1-en-1-ylcarbonyloxy, 2-methylpent-1-en-1-ylcarbonyloxy, 3-methylpent-1-en-1-ylcarbonyloxy, 4-methylpent-1-en-1-ylcarbonyloxy, 1-methylpent-2-en-1-ylcarbonyloxy, 2-methylpent-2-en-1-ylcarbonyloxy, 3-methylpent-2-en-1-ylcarbonyloxy, 4-methylpent-2-en-1-ylcarbonyloxy, 1-methylpent-3-en-1-ylcarbonyloxy, 2-methylpent-3-en-1-ylcarbonyloxy, 3-methylpent-3-en-1-ylcarbonyloxy, 4-methylpent-3-en-1-ylcarbonyloxy, 1-methylpent-4-en-1-ylcarbonyloxy, 2-methylpent-4-en-1-ylcarbonyloxy, 3-methylpent-4-en-1-ylcarbonyloxy, 4-methylpent-4-en-1-ylcarbonyloxy, 1,1-dimethylbut-2-en-1-ylcarbonyloxy, 1,1-dimethylbut-3-en-1-ylcarbonyloxy, 1,2-dimethylbut-3-en-1-ylcarbonyloxy, 1,2-dimethylbut-2-en-1-ylcarbonyloxy, 1,2-dimethylbut-3-en-1-ylcarbonyloxy, 1,3-dimethylbut-3-en-1-ylcarbonyloxy, 1,3-dimethylbut-2-en-1-ylcarbonyloxy, 1,3-dimethylbut-3-en-1-ylcarbonyloxy, 2,2-dimethylbut-3-en-1-ylcarbonyloxy, 2,3-dimethylbut-3-en-1-ylcarbonyloxy, 2,3-dimethylbut-2-en-1-ylcarbonyloxy, 2,3-dimethylbut-3-en-1-ylcarbonyloxy, 3,3-dimethylbut-3-en-1-ylcarbonyloxy, 3,3-dimethylbut-2-en-1-ylcarbonyloxy, 3-ethylbut-1-en-1-ylcarbonyloxy, 1-ethylbut-2-en-1-ylcarbonyloxy, 1-ethylbut-3-en-1-ylcarbonyloxy, 2-ethylbut-3-en-1-ylcarbonyloxy, 2-ethylbut-2-en-1-ylcarbonyloxy, 2-ethylbut-3-en-1-ylcarbonyloxy, 1,1,2-trimethylprop-2-en-1-ylcarbonyloxy, 1-ethyl-1-methylprop-2-en-1-ylcarbonyloxy, 1-ethyl-2-methylprop-1-en-1-ylcarbonyloxy or 1-ethyl-2-methylprop-2-en-1-ylcarbonyloxy, in particular ethenylcarbonyloxy or prop-2-en-1-ylcarbonyloxy;

($C_2$–$C_6$-alkenyl)carbonyloxy-$C_1$–$C_6$-alkyl: $C_1$–$C_6$-alkyl which is substituted by ($C_2$–$C_6$-alkenyl)carbonyloxy, for example 2-propenylcarbonyloxyethyl, 3-propenylcarbonyloxyethyl, 2-propenylcarbonyloxypropyl, 3-propenylcarbonyloxypropyl;

($C_2$–$C_6$-alkynyl)carbonyloxy: ethynylcarbonyloxy, prop-1-yn-1-ylcarbonyloxy, prop-2-yn-1-ylcarbonyloxy, n-but-1-yn-1-ylcarbonyloxy, n-but-1-yn-3-ylcarbonyloxy, n-but-1-yn-4-ylcarbonyloxy, n-but-2-yn-1-ylcarbonyloxy, n-pent-1-yn-1-ylcarbonyloxy, n-pent-1-yn-3-ylcarbonyloxy, n-pent-1-yn-4-ylcarbonyloxy, n-pent-1-yn-5-ylcarbonyloxy, n-pent-2-yn-1-ylcarbonyloxy, n-pent-2-yn-4-ylcarbonyloxy, n-pent-2-yn-5-ylcarbonyloxy, 3-methylbut-1-yn-3-ylcarbonyloxy, 3-methylbut-1-yn-4-ylcarbonyloxy, n-hex-1-yn-1-ylcarbonyloxy, n-hex-1-yn-3-ylcarbonyloxy, n-hex-1-yn-4-ylcarbonyloxy, n-hex-1-yn-5-ylcarbonyloxy, n-hex-1-yn-6-ylcarbonyloxy, n-hex-2-yn-1-ylcarbonyloxy, n-hex-2-yn-4-ylcarbonyloxy, n-hex-2-yn-5-ylcarbonyloxy, n-hex-2-yn-6-ylcarbonyloxy, n-hex-3-yn-1-ylcarbonyloxy, n-hex-3-yn-2-ylcarbonyloxy, 3-methylpent-1-yn-1n-ylcarbonyloxy, 3-methylpent-1-yn-3-ylcarbonyloxy, 3-methylpent-1-yn-4-ylcarbonyloxy, 3-methylpent-1-yn-5-ylcarbonyloxy, 4-methylpent-1-yn-1-ylcarbonyloxy, 4-methylpent-2-yn-4-ylcarbonyloxy or 4-methylpent-2-yn-5-ylcarbonyloxy, in particular ethynylcarbonyloxy or prop-2-yn-1-ylcarbonyloxy;

($C_2$–$C_6$-alkynyl)carbonyloxy-$C_1$–$C_6$-alkyl: $C_1$–$C_6$-alkyl which is substituted by ($C_2$–$C_6$-alkynyl)carbonyloxy, for example 2-propynylcarbonyloxyethyl, 3-propynylcarbonyloxyethyl, 2-propynylcarbonyloxypropyl, 3-propynylcarbonyloxypropyl; Cyano-$C_1$–$C_6$-alkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, in particular cyanomethyl or 2-cyanoethyl;

Nitro-$C_1$–$C_6$-alkyl: for example nitromethyl, 1-nitroeth-1-yl, 2-nitroeth-1-yl, 1-nitroprop-1-yl, 2-nitroprop-1-yl, 3-nitroprop-1-yl, 1-nitroprop-2-yl, 2-nitroprop-2-yl, 1-nitrobut-1-yl, 2-nitrobut-1-yl, 3-nitrobut-1-yl, 4-nitrobut-1-yl, 1-nitrobut-2-yl, 2-nitrobut-2-yl, 1-nitrobut-3-yl, 2-nitrobut-3-yl, 1-nitro-2-methylprop-3-yl, 2-nitro-2-methylprop-3-yl, 3-nitro-2-inethylprop-3-yl or 2-nitromethylprop-2-yl, in particular nitromethyl or 2-nitroethyl;

Hydroxy-$C_1$–$C_4$-alkyl: $CH_2OH$, 1-hydroxyethyl, 2-hydroxyethyl, 1-hydroxyprop-1-yl, 2-hydroxyprop-1-yl, 3-hydroxyprop-1-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 3-hydroxybut-2-yl, 4-hydroxybut-2-yl, 1-($CH_2OH$)eth-1-yl, 1-($CH_2OH$)-1-($CH_3$)-eth-1-yl or 1-($CH_2OH$)prop-1-yl;

Phenyl-$C_1$–$C_6$-alkyl: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)eth-1-yl or 1-(phenylmethyl)prop-1-yl, in particular benzyl or 2-phenylethyl;

Phenoxy-$C_1$–$C_6$-alkyl: for example phenoxymethyl, 1-phenoxyethyl, 2-phenoxyethyl, 1-phenoxyprop-1-yl, 2-phenoxyprop-1-yl, 3-phenoxyprop-1-yl, 1-phenoxybut-1-yl, 2-phenoxybut-1-yl, 3-phenoxybut-1-yl, 4-phenoxybut-1-yl, 1-phenoxybut-2-yl, 2-phenoxybut-2-yl, 3-phenoxybut-2-yl, 4-phenoxybut-2-yl, 1-(phenoxymethyl)eth-1-yl, 1-(phenoxymethyl)-1-(methyl)eth-1-yl or 1-(phenoxymethyl)prop-1-yl, in particular benzyloxy or 2-phenoxyethyl;

Benzyloxy-$C_1$–$C_6$-alkyl: for example benzyloxymethyl, 1-benzyloxyethyl, 2-benzyloxyethyl, 1-benzyloxyprop-1-yl, 2-benzyloxyprop-1-yl, 3-benzyloxyprop-1-yl, 1-benzyloxybut-1-yl, 2-benzyloxybut-1-yl, 3-benzyloxybut-1-yl, 4-benzyloxybut-1-yl, 1-benzyloxybut-2-yl, 2-benzyloxybut-2-yl, 3-benzyloxybut-2-yl, 4-benzyloxybut-2-yl, 1-(benzyloxymethyl)eth-1-yl, 1-(benzyloxymethyl)-1-(methyl)eth-1-yl or 1-(benzyloxymethyl)prop-1-yl, in particular benzyloxy or 2-benzyloxyethyl;

$C_1$–$C_4$-alkylamino: $H_3C$—NH—, $H_5C_2$—NH—, n-propyl-NH—, 1-methylethyl-NH—, n-butyl-NH—, 1-methylpropyl-NH—, 2-methylpropyl-NH— and 1,1-dimethylethyl-NH—, preferably $H_3C$—NH— or $H_5C_2$—NH—, $C_1$–$C_4$-alkylamino-$C_1$–$C_4$-alkyl: $C_1$–$C_4$-alkyl which is substituted by $C_1$–$C_4$-alkylamino as defined above, i.e., for example, $CH_2CH_2$—NH—$CH_3$, $CH_2CH_2$—N($CH_3$)$_2$, $CH_2CH_2$—NH—$C_2H_5$ or $CH_2CH_2$—N($C_2H_5$)$_2$;

Di($C_1$–$C_4$-alkyl)amino: N($CH_3$)$_2$, N($C_2H_5$)$_2$, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably N($CH_3$)$_2$ or N($C_2H_5$)$_2$;

Di($C_1$–$C_4$-alkyl)amino-$C_1$–$C_4$-alkyl: $C_1$–$C_4$-alkyl which is substituted by di($C_1$–$C_4$-alkyl)amino as mentioned above, i.e., for example, $CH_2N(CH_3)_2$, $CH_2N(C_2H_5)_2$, N,N-dipropylaminomethyl, N,N-di[$CH(CH_3)_2$]aminomethyl, N,N-dibutylaminomethyl, N,N-di(1-methylpropyl)aminomethyl, N,N-di(2-methylpropyl)aminomethyl, N,N-di[$C(CH_3)_3$]-aminomethyl, N-ethyl-N-methylaminomethyl, N-methyl-N-propylaminomethyl, N-methyl-N-[$CH(CH_3)_2$]-aminomethyl, N-butyl-N-methylaminomethyl, N-methyl-N-(1-methylpropyl)aminomethyl, N-methyl-N-(2-methylpropyl)aminomethyl, N-[$C(CH_3)_3$]-N-methylaminometh ethyl-N-propylaminomethyl, N-ethyl-N-[$CH(CH_3)_2$]-aminomethyl, N-butyl-N-ethylaminomethyl, N-ethyl-N-(1-methylpropyl)aminomethyl, N-ethyl-N-(2-methylpropyl)aminomethyl, N-ethyl-N-[$C(CH_3)_3$]-aminomethyl, N-[$CH(CH_3)_2$]-N-propylaminomethyl, N-butyl-N-propylaminomethyl, N-(1-methylpropyl)-N-propylaminomethyl, N-(2-methylpropyl)-N-propylaminomethyl, N-[$C(CH_3)_3$]-N-propylaminomethyl, N-butyl-N-(1-methylethyl)aminomethyl, N-[$CH(CH_3)_2$]-N-(1-methylpropyl)aminomethyl, N-[$CH(CH_3)_2$]-N-(2-methylpropyl)aminomethyl, N-[$C(CH_3)_3$]-N-[$CH(CH_3)_2$]-aminomethyl, N-butyl-N-(1-methylpropyl)aminomethyl, N-butyl-N-(2-methylpropyl)aminomethyl, N-butyl-N-[$C(CH_3)_3$]-aminomethyl, N-(1-methylpropyl)-N-(2-methylpropyl)aminomethyl, N-[$C(CH_3)_3$]-N-(1-methylpropyl)aminomethyl, N-[$C(CH_3)_3$]-N-(2-methylpropyl)aminomethyl, N,N-dimethylaminoethyl, N,N-diethylaminoethyl, N,N-di(n-propyl)aminoethyl, N,N-di[$CH(CH_3)_2$]-aminoethyl, N,N-dibutylaminoethyl, N,N-di(1-methylpropyl)aminoethyl, N,N-di(2-methylpropyl)aminoethyl, N,N-di[$C(CH_3)_3$]-aminoethyl, N-ethyl-N-methylaminoethyl, N-methyl-N-propylaminoethyl, N-methyl-N-[$CH(CH_3)_2$]-aminoethyl, N-butyl-N-methylaminoethyl, N-methyl-N-(1-methylpropyl)aminoethyl, N-methyl-N-(2-methylpropyl)aminoethyl, N-[$C(CH_3)_3$]-N-methylaminoethyl, N-ethyl-N-propylaminoethyl, N-ethyl-N-[$CH(CH_3)_2$]-aminoethyl, N-butyl-N-ethylaminoethyl, N-ethyl-N-(1-methylpropyl)aminoethyl, N-ethyl-N-(2-methylpropyl)aminoethyl, N-ethyl-N-[$C(CH_3)_3$]-aminoethyl, N—[$CH(CH_3)_2$]-N-propylaminoethyl, N-butyl-N-propylaminoethyl, N-(1-methylpropyl)-N-propylaminoethyl, N-(2-methylpropyl)-N-propylaminoethyl, N-[$C(CH_3)_3$]-N-propylaminoethyl, N-butyl-N-[$CH(CH_3)_2$]-aminoethyl, N-[$CH(CH_3)_2$]-N-(1-methylpropyl)aminoethyl, N-[$CH(CH_3)_2$]-N-(2-methylpropyl)aminoethyl, N-[$C(CH_3)_3$]-N-[$CH(CH_3)_2$]-aminoethyl, N-butyl-N-(1-methylpropyl)aminoethyl, N-butyl-N-(2-methylpropyl)aminoethyl, N-butyl-N-[$C(CH_3)_3$]-aminoethyl, N-(1-methylpropyl)-N-(2-methylpropyl)aminoethyl, N-[$C(CH_3)_3$]-N-(1-methylpropyl)aminoethyl or N-[$C(CH_3)_3$]-N-(2-methylpropyl)aminoethyl, in particular N,N-dimethylaminoethyl or N,N-diethylaminoethyl;

$C_3$–$C_6$-Cycloalkyl: cyclopropyl, cyclobutyl, cyclopentyl or cyclohexyl;

$C_3$–$C_6$-Cycloalkylamino: cyclopropylamino, cyclobutylamino, cyclopentylamino or cyclohexylamino;

$C_3$–$C_8$-Cycloalkyl: cyclopropyl, cyclobutyl, cyclopentyl, cyclohexyl, cycloheptyl or cyclooctyl;

$C_3$–$C_8$-Cycloalkoxy: cyclopropyloxy, cyclobutyloxy, cyclopentyloxy, cyclohexyloxy, cycloheptyloxy or cyclooctyloxy;

$C_3$–$C_8$-Cycloalkyl-$C_1$–$C_6$-alkyl: $C_1$–$C_6$-alkyl, preferably $C_1$–$C_4$-alkyl, which is substituted by $C_3$–$C_8$-cycloalkyl, for example cyclopropylmethyl, cyclobutylmethyl, cyclopentylmethyl, cyclohexylmethyl, cycloheptylmethyl, cyclooctylmethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclopentyl)butyl, 4-(cyclohexyl)butyl, 4-(cycloheptyl)butyl, 4-(cyclooctyl)butyl, 5-(cyclopropyl)pentyl, 5-(cyclobutyl)pentyl, 5-(cyclopentyl)pentyl, 5-(cyclohexyl)pentyl, 5-(cycloheptyl)pentyl, 5-(cyclooctyl)pentyl, 6-(cyclopropyl)hexyl, 6-(cyclobutyl)hexyl, 6-(cyclopentyl)hexyl, 6-(cyclohexyl)hexyl, 6-(cycloheptyl)hexyl or 6-(cyclooctyl)hexyl;

$C_3$–$C_8$-Cycloalkyloxy-$C_1$–$C_6$-alkyl: $C_1$–$C_6$-alkyl, preferably $C_1$–$C_4$-alkyl, which is substituted by $C_3$–$C_8$-cycloalkyloxy, for example cyclopropyloxymethyl, 1-cyclopropyloxyethyl, 2-cyclopropyloxyethyl, 1-cyclopropyloxyprop-1-yl, 2-cyclopropyloxyprop-1-yl, 3-cyclopropyloxyprop-1-yl, 1-cyclopropyloxybut-1-yl, 2-cyclopropyloxybut-1-yl, 3-cyclopropyloxybut-1-yl, 4-cyclopropyloxybut-1-yl, 1-cyclopropyloxybut-2-yl, 2-cyclopropyloxybut-2-yl, 3-cyclopropyloxybut-2-yl, 3-cyclopropyloxybut-2-yl, 4-cyclopropyloxybut-2-yl, 1-(cyclopropyloxymethyl)eth-1-yl, 1-(cyclopropyloxymethyl)-1-($CH_3$)-eth-1-yl, 1-(cyclopropylmethyloxy)prop-1-yl, cyclobutyloxymethyl, 1-cyclobutyloxyethyl, 2-cyclobutyloxyethyl, 1-cyclobutyloxyprop-1-yl, 2-cyclobutyloxyprop-1-yl, 3-cyclobutyloxyprop-1-yl, 1-cyclobutyloxybut-1-yl, 2-cyclobutyloxybut-1-yl, 3-cyclobutyloxybut-1-yl, 4-cyclobutyloxybut-1-yl, 1-cyclobutyloxybut-2-yl, 2-cyclobutyloxybut-2-yl, 3-cyclobutyloxybut-2-yl, 3-cyclobutyloxybut-2-yl, 4-cyclobutyloxybut-2-yl, 1-(cyclobutyloxymethyl)eth-1-yl, 1-(cyclobutyloxymethyl)-1-($CH_3$)-eth-1-yl, 1-(cyclobutyloxymethyl)prop-1-yl, cyclopentyloxymethyl, 1-cyclopentyloxyeth yl, 2-cyclopentyloxyethyl, 1-cyclopentyloxyprop-1-yl, 2-cyclopentyloxyprop-1-yl, 3-cyclopentyloxyprop-1-yl, 1-cyclopentyloxybut-1-yl, 2-cyclopentyloxybut-1-yl, 3-cyclopentyloxybut-1-yl, 4-cyclopentyloxybut-1-yl, 1-cyclopentyloxybut-2-yl, 2-cyclopentyloxybut-2-yl, 3-cyclopentyloxybut-2-yl, 3-cyclopentyloxybut-2-yl, 4-cyclopentyloxybut-2-yl, 1-(cyclopentyloxymethyl)eth-1-yl, 1-(cyclopentyloxymethyl)-1-($CH_3$)-eth-1-yl, 1-(cyclopentyloxymethyl)prop-1-yl, cyclohexyloxymethyl, 1-cyclohexyloxyethyl, 2-cyclohexyloxyethyl, 1-cyclohexyloxyprop-1-yl, 2-cyclohexyloxyprop-1-yl, 3-cyclohexyloxyprop-1-yl, 1-cyclohexyloxybut-1-yl, 2-cyclohexyloxybut-1-yl, 3-cyclohexyloxybut-1-yl, 4-cyclohexyloxybut-1-yl, 1-cyclohexyloxybut-2-yl, 2-cyclohexyloxybut-2-yl, 3-cyclohexyloxybut-2-yl, 3-cyclohexyloxybut-2-yl, 4-cyclohexyloxybut-2-yl, 1-(cyclohexyloxymethyl)eth-1-yl, 1-(cyclohexyloxymethyl)-1-($CH_3$)-eth-1-yl, 1-(cyclohexyloxymethyl)prop-1-yl, cycloheptyloxymethyl, 1-cycloheptyloxyethyl, 2-cycloheptyloxyethyl, 1-cycloheptyloxyprop-1-yl, 2-cycloheptyloxyprop-1-yl, 3-cycloheptyloxyprop-1- yl, 1-cycloheptyloxybut-1-yl, 2-cycloheptyloxybut-1-yl, 3-cycloheptyloxybut-1-yl, 4-cycloheptyloxybut-1-yl, 1-cycloheptyloxybut-2-yl, 2-cycloheptyloxybut-2-yl, 3-cycloheptyloxybut-2-yl, 3-cycloheptyloxybut-2-yl, 4-cycloheptyloxybut-2-yl, 1-(cycloheptyloxymethyl)eth-1-yl, 1-(cycloheptyloxymethyl)-1-($CH_3$)-eth-1-yl, 1-(cycloheptyloxymethyl)prop-1-yl, cyclooctyloxymethyl, 1-cyclooctyloxyethyl, 2-cyclooctyloxyethyl, 1-cyclooctyloxyprop-1-yl, 2-cyclooctyloxyprop-1-yl, 3-cyclooctyloxyprop-1-yl, 1-cyclooctyloxybut-1-yl, 2-cyclooctyloxybut-1-yl, 3-cyclooctyloxybut-1-yl, 4-cyclooctyloxybut-1-yl, 1-cyclooctyloxybut-2-yl, 2-cyclooctyloxybut-2-yl, 3-cyclooctyloxybut-2-yl, 3-cyclooctyloxybut-2-yl, 4-cyclooctyloxybut-2-yl, 1-(cyclooctyloxymethyl)eth-1-yl, 1-(cyclooctyloxymethyl)-1-($CH_3$)-eth-1-yl or 1-(cyclooctyloxymethyl)prop-1-yl, in particular $C_3$–$C_6$-Cycloalkoxymethyl or 2-($C_3$–$C_6$-cycloalkoxy)ethyl.

With a view to the use of the compounds of the formula I according to the invention as herbicides, the variables V, W, Z, $R^1$ and $R^2$ preferably have the following meanings, in each case on their own or in combination.

Z is O or S, in particular O;

V is O;

W is O;

$R^1$ is hydrogen, fluorine or chlorine;

$R^2$ is halogen, in particular fluorine or chlorine, or cyano, very particularly preferably chlorine.

The variable $R^3$ is, for example: hydrogen, $C_1$–$C_6$-alkyl, $C_1$–$C_6$-haloalkyl, nitro-$C_1$–$C_6$-alkyl, cyano-$C_1$–$C_6$-alkyl, hydroxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylideneiminooxy-$C_1$–$C_6$-alkyl, $C_1$–$C_6$-alkylcarbonyl-$C_1$–$C_6$-alkyl, ($C_1$–$C_6$-alkyl)carbonyloxy-$C_1$–$C_6$-alkyl, $C_3$–$C_8$-cycloalkyl, $C_3$–$C_6$-cycloalkyl-$C_1$–$C_6$-alkyl, $C_3$–$C_6$-cycloalkoxy-$C_1$–$C_6$-alkyl, $C_2$–$C_6$-alkenyl, $C_3$–$C_6$-alkynyl, $C_2$–$C_6$-haloalkenyl, $C_3$–$C_6$-haloalkynyl, $C_3$–$C_6$-alkenyloxy-$C_1$–$C_6$-alkyl, $C_3$–$C_6$-alkynyloxy-$C_1$–$C_6$-alkyl, ($C_2$–$C_6$-alkenyl)carbonyloxy-$C_1$–$C_6$-alkyl, ($C_2$–$C_6$-alkynyl)carbonyloxy-$C_1$–$C_6$-alkyl, ($C_3$–$C_6$-alkenyloxy)carbonyl-$C_1$–$C_6$-alkyl, ($C_3$–$C_6$-alkynyloxy)carbonyl-$C_1$–$C_6$-alkyl, $C_1$–$C_6$-alkoxy-$C_1$–$C_6$-alkyl, $C_1$–$C_6$-alkoxyimino-$C_1$–$C_6$-alkyl, $C_1$–$C_6$-alkoxyimino-$C_1$–$C_6$-alkoxy-$C_1$–$C_6$-alkyl, N—($C_1$–$C_6$-alkoxy-$C_1$–$C_6$-alkyl)amino-$C_1$–$C_6$-alkyl, ($C_1$–$C_6$-alkoxy)carbonyl-$C_1$–$C_6$-alkyl, 2,3-dihydrofuryl, 2,5-dihydrofuryl, tetrahydrofuryl, furyl, phenyl, phenyl-$C_1$–$C_6$-alkyl, benzyloxy-$C_1$–$C_6$-alkyl, phenoxy-$C_1$–$C_6$-alkyl or phenylsulfonyl-$C_1$–$C_6$-alkyl, where furyl and the phenyl rings of the 5 last mentioned groups may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy and $C_1$–$C_6$-alkoxycarbonyl, and is in particular the groups mentioned in Table A.

With a view to the herbicidal activity of the compounds of the formula I, the variable $R^3$ preferably has the following meanings:

$R^3$ is hydrogen, $C_1$–$C_6$-alkyl, $C_2$–$C_6$-alkenyl, $C_3$–$C_6$-alkynyl, ($C_1$–$C_6$-alkoxy)carbonyl-$C_1$–$C_6$-alkyl, $C_3$–$C_6$-cycloalkyl, 2,3-dihydrofuryl, 2,5-dihydrofuryl, tetrahydrofuryl, where each of the eight last mentioned groups may carry one, two or three substituents selected from the group consisting of:

halogen, nitro, cyano, hydroxyl, $C_3$–$C_6$-cycloalkyl, $C_1$–$C_6$-alkoxy, $C_1$–$C_6$-alkoxy-$C_1$–$C_6$-alkoxy, $C_3$–$C_6$-alkenyloxy, $C_3$–$C_6$-alkynyloxy, $C_1$–$C_6$-alkylcarbonyl, $C_1$–$C_6$-alkylcarbonyloxy, $C_1$–$C_6$-alkylthio, $C_1$–$C_6$-alkylsulfinyl, $C_1$–$C_6$-alkylsulfonyl, phenyl, benzyloxy, phenoxy or phenylsulfonyl, where the phenyl rings of the four last mentioned groups may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy and $C_1$–$C_6$-alkoxycarbonyl;

is ($C_3$–$C_6$-alkenyloxy)carbonyl-$C_1$–$C_6$-alkyl, ($C_3$–$C_6$-alkynyloxy)carbonyl-$C_1$–$C_6$-alkyl, furyl or phenyl, where furyl and phenyl may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy and $C_1$–$C_6$-alkoxycarbonyl.

Particularly preferably:

$R^3$ is hydrogen, $C_3$–$C_6$-cycloalkyl, in particular $C_1$–$C_4$-alkyl, $C_3$–$C_4$-alkenyl, $C_3$–$C_4$-alkynyl, ($C_1$–$C_4$-alkoxy)carbonyl-$C_1$–$C_4$-alkyl, tetrahydrofuryl, where each of the six last mentioned groups may carry one, two or three, preferably one or two, substituents selected from the group consisting of:

halogen, cyano, $C_1$–$C_4$-alkoxy, $C_3$–$C_4$-alkenyloxy, $C_3$–$C_4$-alkynyloxy, $C_1$–$C_4$-alkylcarbonyl, $C_1$–$C_4$-alkylcarbonyloxy, $C_1$–$C_4$-alkylsulfonyl, in particular from halogen, cyano, $C_1$–$C_4$-alkoxy and $C_1$–$C_4$-alkylcarbonyl, phenylsulfonyl, in particular phenyl, benzyloxy or phenoxy, where the four last mentioned groups may carry one, two or three, in particular one or two, substituents selected from the group consisting of halogen, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl, in particular from halogen, cyano, $C_1$–$C_3$-alkyl, $C_1$–$C_3$-haloalkyl, $C_1$–$C_3$-alkoxy and $C_1$–$C_3$-alkoxycarbonyl;

is $C_1$–$C_4$-alkoxy-$C_1$–$C_3$-alkoxy-$C_2$–$C_3$-alkyl, ($C_3$–$C_4$-alkenyloxy)carbonyl-$C_1$–$C_3$-alkyl, ($C_3$–$C_4$-alkynyloxy)carbonyl-$C_1$–$C_4$-alkyl, furyl or phenyl, where furyl and phenyl may carry one, two or three substituents selected from the group consisting of halogen, nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl.

Examples of preferred radicals $R^3$ are:

hydrogen, $C_1$–$C_6$-alkyl, $C_1$–$C_6$-haloalkyl, nitro-$C_1$–$C_6$-alkyl, cyano-$C_1$–$C_6$-alkyl, hydroxy-$C_1$–$C_6$-alkyl, $C_1$-$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylcarbonyl-$C_1$–$C_6$-alkyl, ($C_1$–$C_6$-alkyl)carbonyloxy-$C_1$–$C_6$-alkyl, $C_3$–$C_6$-cycloalkyl, $C_3$–$C_6$-cycloalkyl-$C_1$–$C_6$-alkyl, $C_3$–$C_6$-cycloalkoxy-$C_1$–$C_6$-alkyl, $C_1$–$C_6$-alkoxy-$C_1$–$C_6$-alkyl, ($C_1$–$C_6$-alkoxy-$C_1$–$C_6$-alkoxy)-$C_1$–$C_6$-alkyl, ($C_1$–$C_6$-alkoxy)carbonyl-$C_1$–$C_6$-alkyl, $C_3$–$C_6$-alkenyl, $C_3$–$C_6$-alkynyl, $C_3$–$C_6$-haloalkenyl, $C_3$–$C_6$-haloalkynyl, $C_3$–$C_6$-alkenyloxy-$C_1$–$C_6$-alkyl, $C_3$–$C_6$-alkynyloxy-$C_1$–$C_6$-alkyl, ($C_2$–$C_6$-alkenyl)carbonyloxy-$C_1$–$C_6$-alkyl, ($C_2$–$C_6$-alkynyl)carbonyloxy-$C_1$–$C_6$-alkyl, ($C_3$–$C_6$-alkenyloxy)carbonyl-$C_1$–$C_6$-alkyl, ($C_3$–$C_6$-alkynyloxy)carbonyl-$C_1$–$C_6$-alkyl;

2,3-dihydrofur-2-yl, 2,5-dihydrofur-2-yl, tetrahydrofur-2-yl, 2,3-dihydrofur-3-yl, 2,5-dihydrofur-3-yl, tetrahydrofur-3-yl, furyl, phenyl, phenyl-$C_1$–$C_6$-alkyl, phenylsulfonyl-$C_1$–$C_6$-alkyl, benzyloxy-$C_1$–$C_6$-alkyl or phenoxy-$C_1$–$C_6$-alkyl, where the phenyl rings of the five last mentioned groups may carry one or two substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy and $C_1$–$C_6$-alkoxycarbonyl;

in particular:

$C_1$–$C_4$-alkyl, $C_1$–$C_4$-haloalkyl, cyano-$C_1$–$C_4$-alkyl, $C_1$–$C_4$-alkylsulfonyl-$C_1$–$C_4$-alkyl, $C_1$–$C_4$-alkylcarbonyl-$C_1$–$C_4$-alkyl, ($C_1$–$C_4$-alkyl)carbonyloxy-$C_1$–$C_4$-alkyl, $C_3$–$C_6$-cycloalkyl, $C_1$–$C_4$-alkoxy-$C_1$–$C_4$-alkyl, ($C_1$–$C_4$-alkoxy-$C_1$–$C_4$-alkoxy)-$C_1$–$C_4$-alkyl, ($C_1$–$C_4$-alkoxy)carbonyl-$C_1$–$C_4$-alkyl, $C_3$–$C_4$-alkenyl, $C_3$–$C_4$-alkynyl, $C_3$–$C_4$-haloalkenyl, $C_3$–$C_4$-haloalkynyl, $C_3$–$C_4$-alkenyloxy-$C_1$–$C_4$-alkyl, $C_3$–$C_4$-alkynyloxy-$C_1$–$C_4$-alkyl, ($C_3$–$C_4$-alkenyloxy)carbonyl-$C_1$–$C_4$-alkyl, ($C_3$–$C_4$-alkynyloxy)carbonyl-$C_1$–$C_4$-alkyl, tetrahydrofur-2-yl, tetrahydrofur-3-yl, furyl, phenyl, phenyl-$C_1$–$C_4$-alkyl, phenylsulfonyl-$C_1$–$C_4$-alkyl, benzyloxy-$C_1$–$C_4$-alkyl or phenoxy-$C_1$–$C_4$-alkyl, where the phenyl rings of the five last mentioned groups may carry one or two substituents selected from the group consisting of halogen, in particular fluorine or chlorine, nitro, cyano, $C_1$–$C_4$-alkyl, in particular methyl, $C_1$–$C_4$-haloalkyl, in particular trifluoromethyl, $C_1$–$C_4$-alkoxy, in particular methoxy, $C_1$–$C_4$-haloalkoxy and $C_1$–$C_4$-alkoxycarbonyl, in particular methoxycarbonyl.

$R^8$ is preferably $C_1$–$C_6$-alkyl and in particular $C_1$–$C_4$-alkyl.

In preferred compounds of formula I, Het is a cycle of the formula II-3, II-7 or II-13 which is attached via an exocyclic imine nitrogen.

In other preferred compounds of the formula I, Het is a cycle of the formula II-4, II-5, II-6, II-10, II-14, II-17 or II-19 which is attached via an imide nitrogen.

In other preferred compounds of the formula I, Het is a nitrogen heterocycle which has at least one carbonyl or thiocarbonyl function and at least one endocyclic hydrazone structure and which is selected from among the radicals of the formulae II-1, II-2, II-11 and II-12, in particular from II-1 and II-2.

In particularly preferred compounds of the formula I, Het is a cycle of the formula II-4, II-5, II-10, II-14, II-17 or II-19 which is attached via an imide nitrogen, in particular a cycle of the formula II-5, II-10 or II-19.

In Het, X is preferably oxygen. X' is likewise preferably oxygen, where in the formula II-10 the variable X' may also preferably be sulfur. Y in the formula II-6 is likewise preferably oxygen. In the formulae II-3, II-7 and II-13, Y is preferably sulfur. Q in the formula II-1 is preferably oxygen.

If ═══ in the formula II-14 denotes a double bond, $R^4$ can be an imino group which corresponds to the amino groups stated for $R^4$, i.e. imino, $C_1$–$C_6$-alkylimino, $C_3$–$C_6$-alkylimino, or an alkylidene group which corresponds to the alkyl groups stated for $R^4$, i.e., for example, $C_1$–$C_6$-alkylidene, $C_1$–$C_6$-haloalkylidene, $C_3$–$C_8$-cycloalkylidene and $C_3$–$C_8$-cycloalkylalkylidene.

In the radicals Het, the variables $R^4$, $R^{4'}$ and $R^{4''}$ independently of one another preferably have the following meanings: hydrogen, $C_1$–$C_6$-alkyl, halogen, amino, $C_1$–$C_6$-haloalkyl, $C_1$–$C_6$-haloalkoxy, $C_1$–$C_6$-haloalkylthio or $C_1$–$C_6$-alkylsulfonyl.

In the radicals Het, the variables $R^5$ and $R^{5'}$ independently of one another preferably have the following meanings: hydrogen, $C_1$–$C_6$-alkyl, amino or $C_1$–$C_6$-haloalkyl.

Preferred compounds of the formula I can also have radicals Het in which two of the radicals $R^4$, $R^{4'}$, $R^{4''}$, $R^5$ and $R^{5'}$ together with the ring atoms of the cycle Het to which they are attached form a 5-, 6-or 7-membered ring which may be mono- or diunsaturated, fully unsaturated or saturated, which may contain one or two heteroatoms selected from the group consisting of nitrogen, oxygen and sulfur as ring member and which may have one or two substituents selected from the group consisting of $C_1$–$C_4$-alkyl, $C_1$–$C_4$-alkoxy and halogen. Among these, preference is given to those heterocyclic groups in which two adjacent radicals $R^4$, $R^{4'}$ and $R^{4''}$ together with the ring carbon atoms of Het form a 5-, 6- or 7-membered carbocycle and preferably a phenyl, cyclopentane, cyclopentene, cyclohexane or cyclohexene ring which may be substituted in the manner described above; or in which in each case one radical $R^4$ or $R^{4'}$ and one radical $R^5$ or $R^{5'}$ together with the ring atoms of Het form a 5-, 6-or 7-membered azaheterocycle, for example a pyrrolidine, imidazolidine ring, oxazolidine ring, tetra- or hexahydropyridine ring (piperidine ring) which may be substituted in the manner described above; or in which two adjacent radicals $R^5$ and $R^{5'}$ together with the ring nitrogen atoms of Het form a 5-, 6-or 7-membered diazaheterocycle, for example a pyrazoline ring, a tetrahydrodiazine ring or a hexahydrodiazine ring which may be substituted in the manner described above.

Among the compounds of the formula I in which Het is a cycle of the formula II-1, preference is given to those compounds in which X in the formula II-1 is oxygen. In these compounds, Q is preferably likewise oxygen. In these compounds, $R^4$ is preferably $C_1$–$C_4$-alkyl and in particular tert-butyl.

Among the compounds of the formula I in which Het is a cycle of the formula II-2, preference is given to those compounds in which X is oxygen. $R^4$ and $R^5$ are preferably selected from the group consisting of $C_1$–$C_4$-alkyl, in particular methyl, amino and $C_1$–$C_4$-haloalkyl, in particular trifluoromethyl, or together with the ring atoms to which they are attached form a piperidine ring.

Among the compounds of the formula I in which Het is a cycle of the formula II-3, preference is given to those compounds in which X is oxygen. Y is preferably S. Preferably, $R^5$ and $R^{5'}$ together with the nitrogen atoms to which they are attached form a hexahydrodiazine ring.

Among the compounds of the formula I in which Het is a cycle of the formula II-4, preference is given to those compounds in which X and X' are oxygen. Preferably, $R^5$ and $R^{5'}$ together with the nitrogen atoms to which they are attached form a hexahydrodiazine ring.

Among the compounds of the formula I in which Het is a cycle of the formula II-5, preference is given to those compounds in which X and X' are oxygen and $R^4$ and $R^{4'}$ together with the carbon atoms to which they are attached form a cyclohexene ring.

Among the compounds of the formula I in which Het is a cycle of the formula II-6, preference is given to those compounds in which X, X' and Y are oxygen. $R^6$ and $R^7$ are preferably $C_1$–$C_4$-alkyl or, together with the carbon atoms to which they are attached, form a cyclohexane ring.

Among the compounds of the formula I in which Het is a cycle of the formula II-7, preference is given to those compounds in which Y is S. In II-7, $R^4$ and $R^5$ preferably form a 1,3-propylene unit which may have one or 2 methyl groups.

Among the compounds of the formula I in which Het is a cycle of the formula II-8, preference is given to those compounds in which X is oxygen. In II-8, $R^5$ is preferably $C_1$–$C_4$-haloalkyl and in particular trifluoromethyl.

Examples of radicals Het of the formula II-9 are those in which $R^{4'}$ and $R^{4''}$ together with the carbon atoms to which they are attached form a cyclohexane ring. In the radicals II-9, $R^4$ is preferably halogen, in particular chlorine.

Among the compounds of the formula I in which Het is a cycle of the formula II-10, preference is given to those compounds in which the variable X is oxygen and the variable X' is sulfur. In II-10, $R^5$ and $R^{5'}$ independently of one another are preferably hydrogen or $C_1$–$C_4$-alkyl, in particular methyl.

Among the compounds of the formula I in which Het is a cycle of the formula II-11, preference is given to those compounds in which the variables X and X' are oxygen. $R^4$ is preferably hydrogen and $R^5$ is preferably $C_1$–$C_4$-alkyl, in particular methyl, amino or $C_1$–$C_4$-haloalkyl, such as trifluoromethyl and difluoromethyl.

Among the compounds of the formula I in which Het is a cycle of the formula II-12, preference is given to those compounds in which the variable X is oxygen. $R^{4''}$ is preferably hydrogen. $R^4$ and $R^{4'}$ independently of one another are preferably $C_1$–$C_4$-alkyl, in particular methyl, or $C_1$–$C_4$-haloalkyl, in particular trifluoromethyl and difluoromethyl.

Among the compounds of the formula I in which Het is a cycle of the formula II-13, preference is given to those compounds in which X is oxygen. Y is preferably S. Preferably, $R^4$ and $R^{4'}$ together with the carbon atoms to which they are attached form a cyclohexene ring.

Among the compounds of the formula I in which Het is a cycle of the formula II-14, preference is given to those compounds in which X and X' are oxygen. $R^4$ and $R^5$ preferably form, together with the ring atoms of Het to which are attached, a 1,2,3,4-tetrahydropyridine ring.

Among the compounds of the formula I in which Het is a cycle of the formula II-16, preference is given to those compounds in which X and X' are oxygen. $R^5$ and $R^{5'}$ are preferably selected from the group consisting of $C_1$–$C_4$-alkyl, in particular methyl, amino and $C_1$–$C_4$-haloalkyl. $R^5$ is particularly preferably amino. $R^{5'}$ is particularly preferably $C_1$–$C_4$-alkyl, in particular methyl.

Among the compounds of the formula I in which Het is a cycle of the formula II-17, preference is given to those compounds in which X and X' are oxygen. $R^4$ and $R^5$ are preferably selected from the group consisting of $C_1$–$C_4$-alkyl, in particular methyl or ethyl, amino and $C_1$–$C_4$-haloalkyl, in particular difluoromethyl and trifluoromethyl.

Among the compounds of the formula I in which Het is a cycle of the formula II-18, preference is given to those compounds in which X is oxygen. $R^4$ and $R^{4'}$ are preferably selected from the group consisting of $C_1$–$C_4$-alkyl, in particular methyl or ethyl, amino and $C_1$–$C_4$-haloalkyl, in particular difluoromethyl and trifluoromethyl.

Among the compounds of the formula I in which Het is a cycle of the formula II-19, preference is given to those compounds in which X and X' are oxygen. Furthermore, the substituents $R^4$ are preferably selected from the group consisting of $C_1$–$C_4$-alkyl, in particular methyl, and $C_1$–$C_4$-haloalkyl, in particular difluoromethyl and trifluoromethyl. Here, $R^{4'}$ is preferably hydrogen. $R^5$ is preferably selected from the group consisting of $C_1$–$C_4$-alkyl, in particular methyl, $C_1$–$C_4$-haloalkyl, in particular trifluoromethyl, and amino.

Examples of preferred compounds of the formula I are those of the formula I-1 defined below in which Het has one of the meanings mentioned above and $R^3$ has one of the meanings mentioned in Table A, rows 1 to 199.

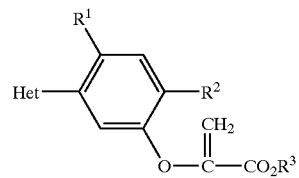

TABLE A

| No. | $R^3$ |
|---|---|
| 1 | H |
| 2 | $CH_3$ |
| 3 | $C_2H_5$ |
| 4 | n-$C_3H_7$ |
| 5 | i-$C_3H_7$ |
| 6 | c-$C_3H_5$ |
| 7 | n-$C_4H_9$ |
| 8 | sec-$C_4H_9$ |
| 9 | i-$C_4H_9$ |
| 10 | tert-$C_4H_9$ |
| 11 | n-$C_5H_{11}$ |
| 12 | $CH_2CH_2CH(CH_3)_2$ |
| 13 | $CH(C_2H_5)_2$ |
| 14 | $CH_2C(CH_3)_3$ |
| 15 | n-$C_6H_{13}$ |
| 16 | sec-$C_6H_{13}$ |
| 17 | $CH_2CH_2CH(CH_3)C_2H_5$ |
| 18 | $CH(C_2H_5)CH_2$—$CH_2CH_3$ |
| 19 | $CH_2$—$CH$=$CH_2$ |
| 20 | $CH_2CH$=$CH$—$CH_3$ |
| 21 | $CH_2$—$C(CH_3)$=$CH_2$ |
| 22 | $C(CH_3)$=$CH$—$CH_3$ |
| 23 | $CH_2CH_2$—$CH$=$CH_2$ |
| 24 | $CH_2$—$CH$=$CH$-$C_2H_5$ |
| 25 | $CH_2$—$CH_2$—$CH$=$CH$—$CH_3$ |
| 26 | $(CH_2)_3CH$=$CH_2$ |
| 27 | $C(CH_3)$=$CH$—$C_2H_5$ |
| 28 | $(CH_2)_4CH$=$CH_2$ |
| 29 | $CH(CH_3)$—$CH$=$CH$—$C_2H_5$ |
| 30 | $CH_2$—$C(CH_3)$=$CH$—$C_2H_5$ |
| 31 | $CH_2C$≡$CH$ |
| 32 | $CH_2C$≡$C$—$CH_3$ |
| 33 | $CH_2$—$CH_2$—$C$≡$CH$ |
| 34 | $CH(CH_3)$—$C$≡$CH$ |
| 35 | $CH_2$—$C$≡$C$—$C_2H_5$ |
| 36 | $CH_2CH_2$—$C$≡$C$—$CH_3$ |
| 37 | $(CH_2)_3C$≡$CH$ |
| 38 | $CH(CH_3)$—$C$≡$C$—$CH_3$ |
| 39 | $(CH_2)_4C$≡$CH$ |
| 40 | $CH(CH_3)$—$C$≡$C$—$C_2H_5$ |
| 41 | $CH(CH_3)$—$CH_2$—$C$≡$C$—$CH_3$ |
| 42 | $CH_2$—$C$≡$C$—n-$C_3H_7$ |
| 43 | $CH_2CH_2OCH_3$ |
| 44 | $CH_2CH_2OC_2H_5$ |
| 45 | $CH_2CH_2O$-n$C_3H_7$ |
| 46 | $(CH_2)_2OCH_3$ |
| 47 | $(CH_2)_3OC_2H_5$ |
| 48 | $CH_2CH_2O$—i-$C_3H_7$ |
| 49 | $CH(CH_3)CH_2OCH_3$ |
| 50 | $C(CH_3)_2CH_2OCH_3$ |
| 51 | $CH_2CH$=$N$—$OCH_3$ |
| 52 | $CH_2CH$=$N$—$OC_2H_5$ |
| 53 | $CH_2CH$=$N$—$O$—n-$C_3H_7$ |
| 54 | $CH(CH_3)$—$CH$=$N$—$OCH_3$ |
| 55 | $CH_2CH_2$—$NHCH_2CH_2OCH_3$ |
| 56 | $CH_2CH_2NHCH_2CH_2OC_2H_5$ |
| 57 | $CH(CH_3)CH_2NHCH_2CH_2OCH_3$ |
| 58 | c-$C_4H_7$ |
| 59 | c-$C_5H_9$ |
| 60 | c-$C_6H_{11}$ |
| 61 | 2-furyl |
| 62 | 3-furyl |

TABLE A-continued

| No. | $R^3$ |
|---|---|
| 63 | 2,3-dihydrofur-2-yl |
| 64 | 2,3-dihydrofur-3-yl |
| 65 | 2,5-dihydrofur-2-yl |
| 66 | tetrahydrofur-2-yl |
| 67 | tetrahydrofur-3-yl |
| 68 | $(CH_2)_2Cl$ |
| 69 | $(CH_2)_2$—Br |
| 70 | $(CH_2)_2F$ |
| 71 | $CH(CH_3)CH_2Cl$ |
| 72 | $CH_2CH(CH_3)Cl$ |
| 73 | $CH(CH_3)CH_2Br$ |
| 74 | $(CH_2)_3Cl$ |
| 75 | $(CH_2)_3Br$ |
| 76 | $C(CH_3)_2CH_2Cl$ |
| 77 | $CH_2CF_3$ |
| 78 | $CH_2$—$CF$=$CF_2$ |
| 79 | $CH_2CH_2NO_2$ |
| 80 | $(CH_2)_3NO_2$ |
| 81 | $CH_2CH_2CN$ |
| 82 | $(CH_2)_3CN$ |
| 83 | $CH(CH_3)CN$ |
| 84 | $C(CH_3)_2CN$ |
| 85 | $C(CH_3)_2CH_2CN$ |
| 86 | $CH_2CH_2OH$ |
| 87 | $(CH_2)_3OH$ |
| 88 | $CH(CH_3)CH_2OH$ |
| 89 | $C(CH_3)_2CH_2OH$ |
| 90 | $CH_2$—c-$C_3H_5$ |
| 91 | $CH_2$—c-$C_4H_7$ |
| 92 | $CH_2$—c-$C_5H_9$ |
| 93 | $CH_2$—c-$C_6H_{11}$ |
| 94 | $CH_2CH_2OCH_2CH_2OCH_3$ |
| 95 | $CH_2CH_2OCH_2CH_2OC_2H_5$ |
| 96 | $CH_2CH_2O$—c-$C_4H_7$ |
| 97 | $CH_2CH_2O$—c-$C_5H_9$ |
| 98 | $CH_2CH_2O$—$CH_2CH$=$CH_2$ |
| 99 | $CH(CH_3)CH_2O$—$CH_2CH$=$CH_2$ |
| 100 | $CH_2CH_2$—O—$CH_2$—$CH$=$CH$—$CH_3$ |
| 101 | $CH(CH_3)CH_2O$—$CH_2$—$CH$=$CH$—$CH_3$ |
| 102 | $CH_2CH_2O$—$CH_2$—$C$≡$CH$ |
| 103 | $CH(CH_3)CH_2O$—$CH_2$—$C$≡$CH$ |
| 104 | $CH_2CH_2O$—$CH_2$—$C$≡$C$—$CH_3$ |
| 105 | $CH(CH_3)CH_2O$—$CH_2C$≡$C$—$CH_3$ |
| 106 | $CH_2C(O)CH_3$ |
| 107 | $CH_2CH_2C(O)CH_3$ |
| 108 | $CH_2CH_2O$—$C(O)CH_3$ |
| 109 | $CH_2CH_2O$—$C(O)C_2H_5$ |
| 110 | $(CH_2)_3O$—$C(O)CH_3$ |
| 111 | $CH_2CH_2O$—$C(O)CH_2CH$=$CH_2$ |
| 112 | $CH(CH_3)CH_2O$—$C(O)CH_2CH$=$CH_2$ |
| 113 | $CH_2CH_2O$—$C(O)C(CH_3)$=$CH_2$ |
| 114 | $CH_2CH_2O$—$C(O)CH_2$—$C$≡$CH$ |
| 115 | $CH_2CH_2SCH_3$ |
| 116 | $CH_2CH_2SC_2H_5$ |
| 117 | $(CH_2)_3SCH_3$ |
| 118 | $CH(CH_3)CH_2SCH_3$ |
| 119 | $C(CH_3)_2CH_2SCH_3$ |
| 120 | $CH_2CH_2S(O)CH_3$ |
| 121 | $CH_2CH_2S(O)C_2H_5$ |
| 122 | $CH(CH_3)CH_2S(O)CH_3$ |
| 123 | $C(CH_3)_2CH_2S(O)CH_3$ |
| 124 | $CH_2CH_2SO_2CH_3$ |
| 125 | $(CH_2)_3SO_2CH_3$ |
| 126 | $CH(CH_3)CH_2SO_2CH_3$ |
| 127 | $C(CH_3)_2CH_2SO_2CH_3$ |
| 128 | $CH_2CH_2O$—N=$CH_2$ |
| 129 | $CH_2CH_2O$—N=$CHCH_3$ |
| 130 | $CH_2CH_2O$—N=$CH$—$C_2H_5$ |
| 131 | $CH(CH_3)CH_2O$—N=$CHCH_3$ |
| 132 | $CH_2CH_2O$—$CH_2CH$=$NOCH_3$ |
| 133 | $CH_2CH_2O$—$CH_2CH$=$NOC_2H_5$ |
| 134 | $CH_2C_6H_5$ |
| 135 | $CH_2CH_2C_6H_5$ |
| 136 | 4-chlorobenzyl |
| 137 | 3-chlorobenzyl |
| 138 | 2-chlorobenzyl |
| 139 | 2,4-dichlorobenzyl |
| 140 | 2,4,6-trichlorobenzyl |
| 141 | 2-nitrobenzyl |
| 142 | 3-nitrobenzyl |
| 143 | 4-nitrobenzyl |
| 144 | 2-$CH_3O$—benzyl |
| 145 | 3-$CH_3O$—benzyl |
| 146 | 4-$CH_3O$—benzyl |
| 147 | 2-chloro-4-methoxybenzyl |
| 148 | 4-chloro-2-methoxybenzyl |
| 149 | 3,4-dichlorobenzyl |
| 150 | 4-chloro-3-methoxybenzyl |
| 151 | $(CH_2)_2O$—benzyl |
| 152 | $(CH_2)_2O$—2-chlorobenzyl |
| 153 | $(CH_2)_2O$—3-chlorobenzyl |
| 154 | $(CH_2)_2O$—4-chlorobenzyl |
| 155 | $(CH_2)_2O$—3,4-dichlorobenzyl |
| 156 | $(CH_2)_2O$—3-chloro-4-methoxybenzyl |
| 157 | $CH_2CH_2O$-phenyl |
| 158 | $CH_2CH_2O$—2-chlorophenyl |
| 159 | $CH_2CH_2O$—3-chlorophenyl |
| 160 | $CH_2CH_2O$—4-chlorophenyl |
| 161 | $CH_3CH_2O$—2,3-dichlorophenyl |
| 162 | $CH_2CH_2O$—3,4-dichlorophenyl |
| 163 | $CH_2CH_2O$—4-chloro-3-methoxyphenyl |
| 164 | $CH_2CH_2O$—chloro-4-trifluoromethylphenyl |
| 165 | $CH_2CH_2O$—3-chloro-4-methylphenyl |
| 166 | $CH_2CH_2O$—4-nitrophenyl |
| 167 | $CH_2CH_2O$—3-nitrophenyl |
| 168 | $CH_2CH_2O$—2-nitrophenyl |
| 169 | $CH_2CH_2O$—4-cyanophenyl |
| 170 | $CH_2CH_2O$—3-cyanophenyl |
| 171 | $CH_2CH_2O$—2-cyanophenyl |
| 172 | $CH_2CH_2O$—4-methoxycarbonylphenyl |
| 173 | $CH_2CH_2O$—4-methylphenyl |
| 174 | $CH_2CH_2O$—3-methylphenyl |
| 175 | 4-acetoxytetrahydrofur-3-yl |
| 176 | $C(CH_3)_2CO_2CH_2CH$=$CH_2$ |
| 177 | $C(CH_3)_2CO_2CH_2C$≡$CH$ |
| 178 | phenyl |
| 179 | 2-chlorophenyl |
| 180 | 3-chlorophenyl |
| 181 | 4-chlorophenyl |
| 182 | 2,3-dichlorophenyl |
| 183 | 2-methylphenyl |
| 184 | 3-methylphenyl |
| 185 | 4-methylphenyl |
| 186 | 2-nitrophenyl |
| 187 | 3-nitrophenyl |
| 188 | 4-nitrophenyl |
| 189 | 4-trifluoromethylphenyl |
| 190 | 2-cyanophenyl |
| 191 | 3-cyanophenyl |
| 192 | 4-cyanophenyl |
| 193 | 2-chloro-4-nitrophenyl |
| 194 | 2-chloro-4-cyanophenyl |
| 195 | 2,4-dichlorophenyl |
| 196 | 2-chloro-4-methylphenyl |
| 197 | 3-methoxycarbonylphenyl |
| 198 | 4-methoxycarbonylphenyl |
| 199 | sec-$C_5H_{11}$ | c-$C_nH_{2n-1}$ is cycloalkyl, i-$C_nH_{2n+1}$ is isoalkyl, n-$C_nH_{2n+1}$ is n-alkyl, sec-$C_nH_{2n+1}$ is secondary alkyl and tert-$C_nH_{2n+1}$ is tertiary alkyl.

Preference is given to the compounds of the formula Ia (Compounds Ia$^1$.1 to Ia$^1$.199) in which $R^1$ is fluorine, $R^2$ is chlorine and Z is oxygen and $R^3$ has the meanings mentioned in rows 1 to 199 of Table A.

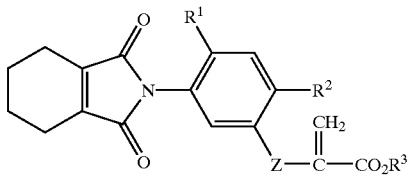

(Ia)

Preference is furthermore given to the compounds of the formula Ia (Compounds $Ia^2.1$ to $Ia^2.199$) in which $R^1$ is fluorine, $R^2$ is chlorine and Z is S and $R^3$ has the meanings mentioned in rows 1 to 199 of Table A.

Preference is given to the compounds of the formula Ia (Compounds $Ia^3.1$ to $Ia^3.199$) in which $R^1$ is hydrogen, $R^2$ is chlorine and Z is oxygen and $R^3$ has the meanings mentioned in rows 1 to 199 of Table A.

Preference is furthermore given to the compounds of the formula Ia (Compounds $Ia^4.1$ to $Ia^4.199$) in which $R^1$ is hydrogen, $R^2$ is chlorine and Z is S and $R^3$ has the meanings mentioned in rows 1 to 199 of Table A.

Preference is given to the compounds of the formula Ia (Compounds $Ia^5.1$ to $Ia^5.199$) in which $R^1$ and $R^2$ are chlorine and Z is oxygen and $R^3$ has the meanings mentioned in rows 1 to 199 of Table A.

Preference is furthermore given to the compounds of the formula Ia (Compounds $Ia^6.1$ to $Ia^6.199$) in which $R^1$ and $R^2$ are chlorine and Z is S and $R^3$ has the meanings mentioned in rows 1 to 199 of Table A.

Preference is given to the compounds of the formula Ib (Compounds $Ib^1.1$ to $Ib^1.199$) in which $R^1$ is fluorine, $R^2$ is chlorine, $R^5$ is methyl and Z is oxygen and $R^3$ has the meanings mentioned in rows 1 to 199 of Table A.

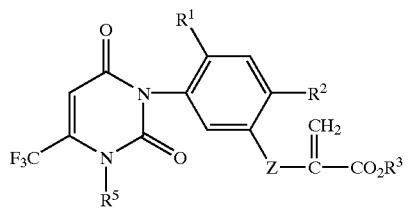

(Ib)

Preference is given to the compounds of the formula Ib (Compounds $Ib^2.1$ to $Ib^2.199$) in which $R^1$ is fluorine, $R^2$ is chlorine, $R^5$ is methyl and Z is sulfur and $R^3$ has the meanings mentioned in rows 1 to 199 of Table A.

Preference is given to the compounds of the formula Ib (Compounds $Ib^3.1$ to $Ib^3.199$) in which $R^1$ is fluorine, $R^2$ is chlorine, $R^5$ is amino and Z is oxygen and $R^3$ has the meanings mentioned in rows 1 to 199 of Table A.

Preference is given to the compounds of the formula Ib (Compounds $Ib^4.1$ to $Ib^4.199$) in which $R^1$ is fluorine, $R^2$ is chlorine, $R^5$ is amino and Z is sulfur and $R^3$ has the meanings mentioned in rows 1 to 199 of Table A.

Preference is given to the compounds of the formula Ib (Compounds $Ib^5.1$ to $Ib^5.199$) in which $R^1$ is hydrogen, $R^2$ is chlorine, $R^5$ is methyl and Z is oxygen and $R^3$ has the meanings mentioned in rows 1 to 199 of Table A.

Preference is given to the compounds of the formula Ib (Compounds $Ib^6.1$ to $Ib^6.199$) in which $R^1$ is hydrogen, $R^2$ is chlorine, $R^5$ is methyl and Z is sulfur and $R^3$ has the meanings mentioned in rows 1 to 199 of Table A.

Preference is given to the compounds of the formula Ib (Compounds $Ib^7.1$ to $Ib^7.199$) in which $R^1$ is hydrogen, $R^2$ is chlorine, $R^5$ is amino and Z is oxygen and $R^3$ has the meanings mentioned in rows 1 to 199 of Table A.

Preference is given to the compounds of the formula Ib (Compounds $Ib^8.1$ to $Ib^8.199$) in which $R^1$ is hydrogen, $R^2$ is chlorine, $R^5$ is amino and Z is sulfur and $R^3$ has the meanings mentioned in rows 1 to 199 of Table A.

Preference is given to the compounds of the formula Ib (Compounds $Ib^9.1$ to $Ib^9.199$) in which $R^1$ and $R^2$ are chlorine, $R^5$ is methyl and Z is oxygen and $R^3$ has the meanings mentioned in rows 1 to 199 of Table A.

Preference is given to the compounds of the formula Ib (Compounds $Ib^{10}.1$ to $Ib^{10}.199$) in which $R^1$ and $R^2$ are chlorine, $R^5$ is methyl and Z is sulfur and $R^3$ has the meanings mentioned in rows 1 to 199 of Table A.

Preference is given to the compounds of the formula Ib (Compounds $Ib^{11}.1$ to $Ib^{11}.199$) in which $R^1$ and $R^2$ are chlorine, $R^5$ is amino and Z is oxygen and $R^3$ has the meanings mentioned in rows 1 to 199 of Table A.

Preference is given to the compounds of the formula Ib (Compounds. $Ib^{12}.1$ to $Ib^{12}.199$) in which $R^1$ and $R^2$ are chlorine, $R^5$ is amino and Z is sulfur and $R^3$ has the meanings mentioned in rows 1 to 199 of Table A.

Preference is also given to the compounds of the formula Ic (Compounds $Ic^1.1$ to $Ic^1.199$) in which $R^3$ has the meanings mentioned in rows 1 to 199 of Table A.

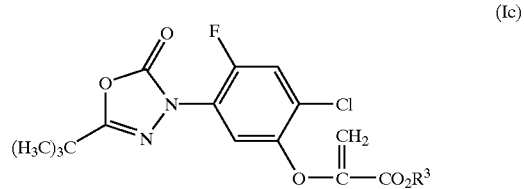

(Ic)

Preference is also given to the compounds of the formula Id (Compounds $Id^1.1$ to $Id^1.199$) in which $R^3$ has the meanings mentioned in rows 1 to 199 of Table A.

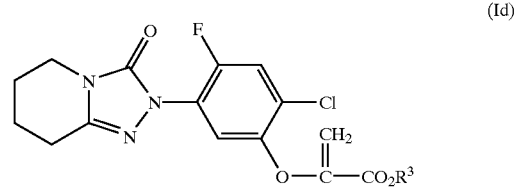

(Id)

Preference is given to the compounds of the formula Ie (Compounds $Ie^1.1$ to $Ie^1.199$) in which Z is oxygen and $R^3$ has the meanings mentioned in rows 1 to 199 of Table A.

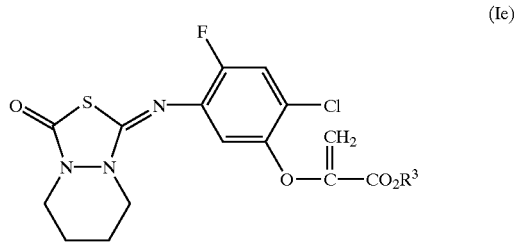

(Ie)

Preference is furthermore given to the compounds of the formula Ie (Compounds $Ie^2.1$ to $Ie^2.199$) in which Z is sulfur and $R^3$ has the meanings mentioned in rows 1 to 199 of Table A.

Preference is also given to the compounds of the formula If (Compounds $If^1.1$ to $If^1.199$) in which $R^3$ has the meanings mentioned in rows 1 to 199 of Table A.

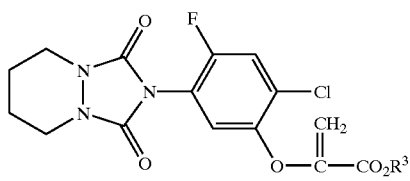
(If)

Preference is also given to the compounds of the formula Ig in which $R^3$ has the meanings mentioned in rows 1 to 199 of Table A.

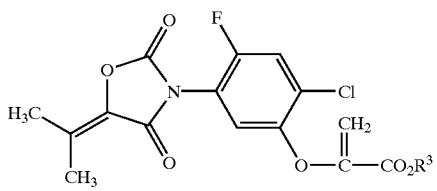
(Ig)

Preference is also given to the compounds of the formula Ih in which $R^3$ has the meanings mentioned in rows 1 to 199 of Table A.

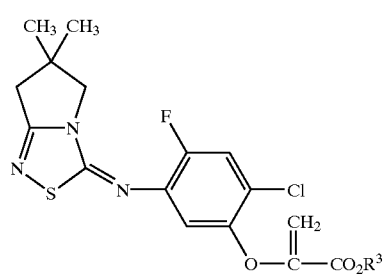
(Ih)

Preference is also given to the compounds of the formula Ii in which $R^3$ has the meanings mentioned in rows 1 to 199 of Table A.

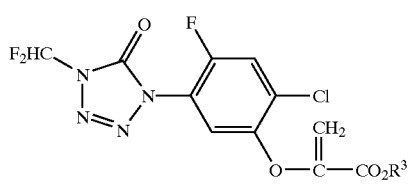
(Ii)

Preference is also given to the compounds of the formula Ij in which $R^3$ has the meanings mentioned in rows 1 to 199 of Table A.

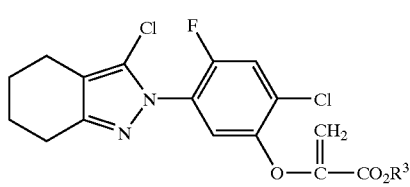
(Ij)

Preference is also given to the compounds of the formula Ik in which $R^3$ has the meanings mentioned in rows 1 to 199 of Table A.

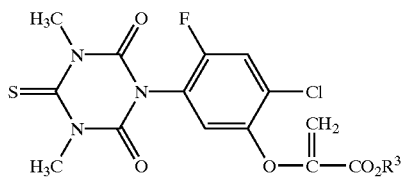
(Ik)

Preference is also given to the compounds of the formula Il in which $R^3$ has the meanings mentioned in rows 1 to 199 of Table A.

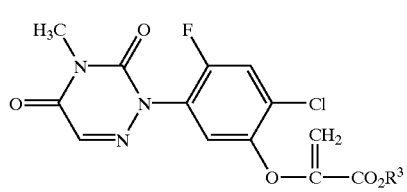
(Il)

Preference is also given to the compounds of the formula Im in which $R^3$ has the meanings mentioned in rows 1 to 199 of Table A.

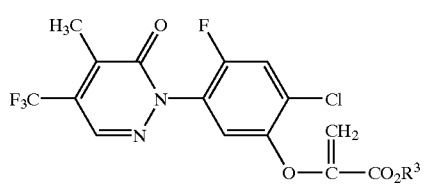
(Im)

Preference is also given to the compounds of the formula In in which $R^3$ has the meanings mentioned in rows 1 to 199 of Table A.

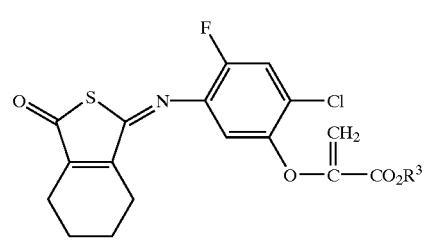
(In)

Preference is also given to the compounds of the formula Io in which $R^3$ has the meanings mentioned in rows 1 to 199 of Table A.

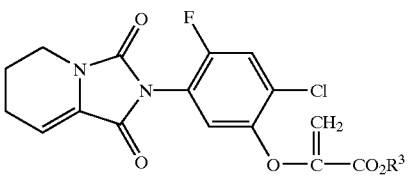
(Io)

Preference is also given to the compounds of the formula Ip in which $R^3$ has the meanings mentioned in rows 1 to 199 of Table A.

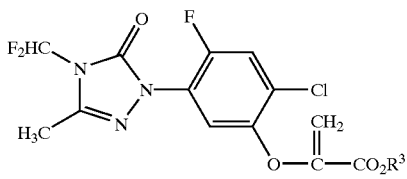
(Ip)

Preference is also given to the compounds of the formula Iq in which $R^3$ has the meanings mentioned in rows 1 to 199 of Table A.

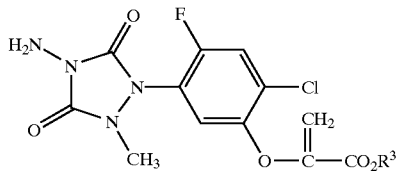
(Iq)

Preference is also given to the compounds of the formula Ir in which $R^3$ has the meanings mentioned in rows 1 to 199 of Table A.

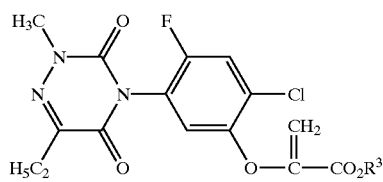
(Ir)

Preference is also given to the compounds of the formula Is in which $R^3$ has the meanings mentioned in rows 1 to 199 of Table A.

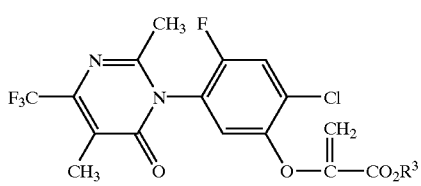
(Is)

Preference is given to the compounds of the formula It (Compounds $It^1.1$ to $It^1.199$) in which $R^1$ is fluorine, $R^2$ is chlorine, $R^5$ is methyl and Z is oxygen and $R^3$ has the meanings mentioned in rows 1 to 199 of Table A.

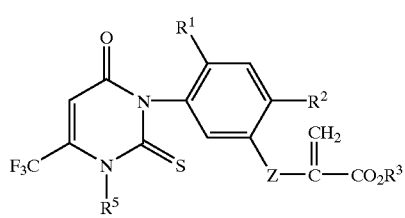
(It)

Preference is given to the compounds of the formula It (Compounds $It^2.1$ to $It^2.199$) in which $R^1$ is fluorine, $R^2$ is chlorine, $R^5$ is methyl and Z is sulfur and $R^3$ has the meanings mentioned in rows 1 to 199 of Table A.

Preference is given to the compounds of the formula It (Compounds $It^3.1$ to $It^3.199$) in which $R^1$ is hydrogen, $R^2$ is chlorine, $R^5$ is methyl and Z is oxygen and $R^3$ has the meanings mentioned in rows 1 to 199 of Table A.

Preference is given to the compounds of the formula It (Compounds $It^4.1$ to $It^4.199$) in which $R^1$ is hydrogen, $R^2$ is chlorine, $R^5$ is methyl and Z is sulfur and $R^3$ has the meanings mentioned in rows 1 to 199 of Table A.

Preference is given to the compounds of the formula It (Compounds $It^5.1$ to $It^5.199$) in which $R^1$ and $R^2$ are chlorine, $R^5$ is methyl and Z is oxygen and $R^3$ has the meanings mentioned in rows 1 to 199 of Table A.

Preference is given to the compounds of the formula It (Compounds $It^6.1$ to $It^6.199$) in which $R^1$ and $R^2$ are chlorine, $R^5$ is methyl and Z is sulfur and $R^3$ has the meanings mentioned in rows 1 to 199 of Table A.

The compounds of the formula I according to the invention are advantageously prepared by synthesizing the heterocycle in question starting from the compounds of the formula III $$\underset{\substack{R^y \\ \\ }}{\overset{R^1}{\underset{\substack{| \\ }}{\bigcirc}}} \quad \text{(III)}$$

in which $R^1$, $R^2$, $R^3$, V, W and Z are as defined in claim 1 and $-R^y$ is $-N=C=O$, $-N=C=S$, $-NH-NH_2$, $NO_2$ or a group $-NH-R^{10}$ in which $R^{10}$ is hydrogen or $C_1-C_6$-alkylcarbonyl. Among the compounds of the formula III, preference is given to those compounds in which Z, V and W are oxygen and $R^3$ is selected from the group consisting of hydrogen, $C_1-C_6$-alkyl, $C_1-C_6$-haloalkyl, $C_1-C_6$-cyanoalkyl, $C_1-C_6$-alkoxy-$C_1-C_6$-alkyl, $C_2-C_6$-alkenyl, $C_2-C_6$-alkynyl, $C_3-C_6$-cycloalkyl, ($C_1-C_6$-alkoxy)carbonyl-$C_1-C_6$-alkyl and phenyl which may carry one, two or three substituents selected from the group consisting of halogen, cyano, $C_1-C_6$-alkyl, $C_1-C_6$-haloalkyl, $C_1-C_6$-alkoxy, $C_1-C_6$-haloalkoxy and $C_1-C_6$-alkoxycarbonyl. $R^3$ is particularly preferably selected from the group consisting of hydrogen, $C_1-C_6$-alkyl, $C_1-C_6$-haloalkyl and $C_1-C_6$-cyanoalkyl. The compounds of the formula III are novel and, as useful intermediates for the preparation of I, likewise form part of the subject matter of the present invention.

Depending on the nature of the heterocyclic radical Het, the synthesis is carried out starting from the respective aniline IIIa ($R^y=NHR^{10}$), the phenyl isocyanate IIIc ($R^y=N=C=O$), the corresponding phenyl isothiocyanate IIId ($R^y=N=C=S$) or the hydrazine IIIe ($R^y=NH-NH_2$). The iso(thio)cyanates IIIb and IIId are, like the hydrazine IIIa, generally prepared starting from the respective aniline IIIa' ($R^y=NH_2$) which for its part is obtainable by reducing the corresponding nitro compound IIIb ($R^y=NO_2$).

The conversion of the nitro compounds IIIb into the aniline derivatives IIIa is carried out, for example, using hydrogen in the presence of a hydrogenation catalyst, for example a metal catalyst, such as Raney nickel.

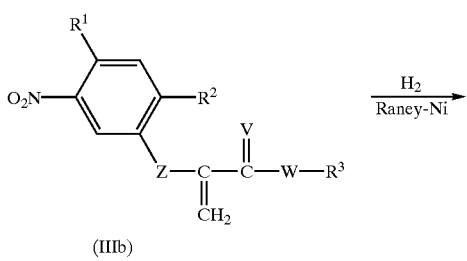

(IIIb)

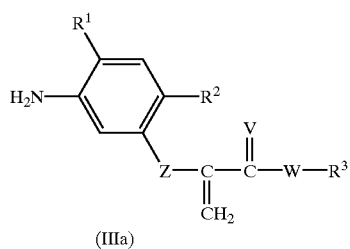

(IIIa)

The reduction is advantageously carried out in an inert polar solvent or diluent, for example an ether, such as tetrahydrofuran, an amide, such as dimethylformamide, an aliphatic $C_1$–$C_4$-carboxylic acid, such as acetic and propionic acid, the ester of an aliphatic $C_1$–$C_4$-carboxylic acid, such as ethyl acetate, or an alcohol, in particular in methanol or ethanol.

The amount of catalyst is not critical; usually, from 0.1 to 50 mol %, in particular from 0.5 to 5 mol %, based on the amount of nitro compound IIIb, are used. The hydrogenation is advantageously carried out at a partial hydrogen pressure in the range from 0.5 to 100 bar, preferably in the range from 1 to 10 bar. In general, the reaction is carried out at temperatures of at least 0° C., and the upper limit of the reaction temperature is generally given by the boiling point of the solvent in question. Work-up of the reaction mixture is carried out by customary methods.

The process can be carried out both batchwise and continuously. In the continuous procedure, the nitro compound IIIb is, in a solution which is saturated with hydrogen, preferably passed over a fixed bed which has been covered with the catalyst.

In a preferred embodiment, hydrogen is added to a mixture of the nitro compound IIIb, diluent (solvent) and catalyst until no more hydrogen is consumed.

The reduction of IIIb to IIIa can also be carried out using nascent hydrogen. To this end, the nitro compound IIIb is reacted with iron powder in an inorganic acid example hydrochloric acid, or in a mixture of inorganic acid and one of the abovementioned solvents, for example an ether, or in an organic carboxylic acid, advantageously acetic acid. The reduction is generally carried out at 20 to 120° C., advantageously at 50 to 80° C.

The nitro compound IIIb can be prepared by the method of the process described in U.S. Pat. No. 3,402,198 by reacting a substituted phenol (Z=O) or a thiophenol (Z=S) of the formula VI with a 2-haloacrylic acid ester derivative of the formula VII in which Hal is halogen, in particular chlorine or bromine, and specifically bromine. In the formulae IIIb, VI and VII, $R^1$, $R^2$ and $R^3$ and V, W and Z are as defined above. V and W are preferably oxygen (Compounds VIa and IIIb'). The conversion of the esters IIIb' (V=W=O) into the corresponding thioesters of IIIb (W=S and/or V=S) is carried out by known methods (see, for example, Houben-Weyl, Methoden der Organischen Chemie [Methods of Organic Chemistry], IVth edition, Volume E5, thiocarboxylic acid O-esters, pp. 785–801; ibid thiocarboxylic acid S-esters, pp. 849–883; ibid dithiocarboxylic esters, pp. 891–916). Carboxylic acid derivatives can be sulfurized in an advantageous manner using Lawesson's reagent (see R. Shabana, J. B. Rasmussen, S. O. Olesen, S. O. Lawesson in Tetrahedron 36 (1980), 3047–3051; J. B. Rasmussen, R. Shabana and S. O. Lawesson, Tetrahedron 37 (1981), 197–206).

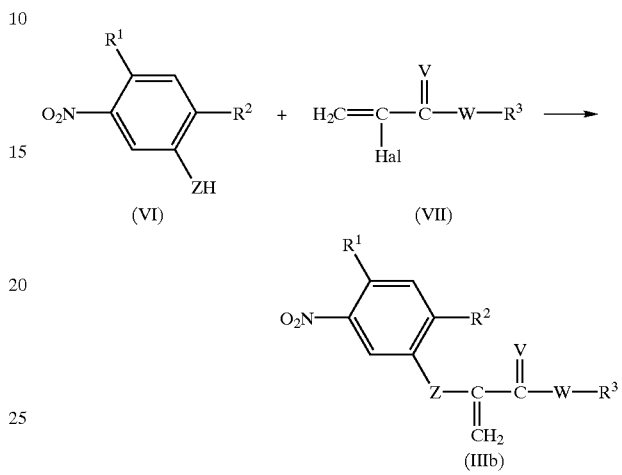

Correspondingly, it is also possible to react a protected aniline derivative VIII in which $R^{10}$ is $C_1$–$C_6$-alkylcarbonyl, such as acetyl, with a haloacrylic acid ester derivative of the formula VII to give the corresponding protected aniline derivative of the formula IIIa. In the formulae IIIa, VII and VIII, $R^1$, $R^2$ and $R^3$ and V, W and Z are as defined above. In VI and IIIa, V and W are preferably oxygen (Compounds VIa and IIIa'). The conversion of the esters IIIa' (V=W=O) into the corresponding thioesters of IIIa (W=S and/or V=S) is carried out by known methods (see above).

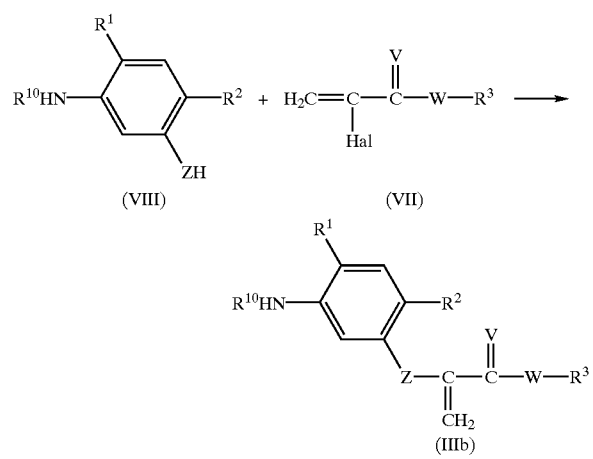

Surprisingly, it has now been found that nitro(thio)phenoxydihalopropionic esters of the formula IV, in particular the dichloro and the dibromo compounds, can be dehalogenated with reduction of the nitro group to give the aniline derivatives of the formula V. Accordingly, the present invention also relates to a process for preparing compounds of the formula V

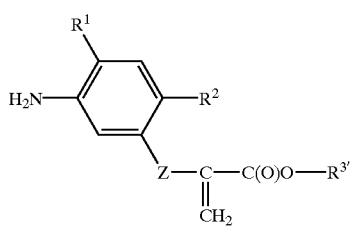

which comprises reacting a compound of the formula IV

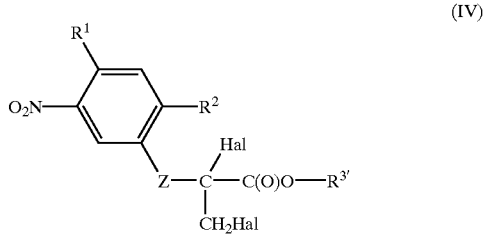

with nascent hydrogen.

In the formulae IV and V, $R^1$, $R^2$ and Z are as defined above and $R^{3'}$ is hydrogen, $C_1$–$C_6$-alkyl, $C_3$–$C_6$-cycloalkyl, $C_1$–$C_6$-haloalkyl, $C_1$–$C_6$-cyanoalkyl, $C_1$–$C_6$-alkoxy-$C_1$–$C_6$-alkyl, ($C_1$–$C_6$-alkoxy)carbonyl-$C_1$–$C_6$-alkyl or phenyl which may carry one, two or three substituents selected from the group consisting of halogen, cyano, $C_1$–$C_6$-alkyl, $C_1$–$C_6$-haloalkyl, $C_1$–$C_6$-alkoxy, $C_1$–$C_6$-haloalkoxy and $C_1$–$C_6$-alkoxycarbonyl. Hal in the formula IV is halogen, preferably chlorine or bromine and in particular bromine.

The compounds of the formula V correspond to the compound IIIa (where V=W=O and $R^3$=$R^{3'}$) and can be converted by the abovementioned methods into other esters of IIIa and into the thiocarbonyl compounds and the thioesters of IIIa (W=S and/or V=S). The compounds of the formulae IV and V are useful intermediates for the preparation of compounds I and therefore likewise form part of the subject matter of the present invention.

The conversion of IV into V is carried out according to the invention using nascent hydrogen. To this end, the nitro compound IV is reacted with an acid in the presence of a base metal. According to their nature, base metals are metals which are dissolved by a Brønsted acid with evolution of hydrogen. Such metals generally have a normal potential of <0. Examples of suitable metals are Zn, Fe and Sn, in particular Fe. Acids which are suitable for this purpose are both inorganic mineral acids, for example hydrochloric acid or dilute sulfuric acid, or mixtures of inorganic acid and one of the abovementioned solvents, for example gaseous HCl in an ether or an alcohol, or a mixture thereof, and organic carboxylic acids, advantageously acetic acid, propionic acid or butyric acid.

Essentially, the reaction conditions correspond to the reaction conditions used for the reduction of aliphatic or aromatic nitro groups to aliphatic or aromatic amino groups with nascent hydrogen (see, for example, H. Koopman, Rec. Trav. 80 (1961), 1075; see also N. Kornblum, L. Fischbein, J. Am. Chem. Soc. 77, (1955), 6266).

Depending on the type of metal and acid, the reaction temperature is generally in the range from −20 to +120° C., and, if alkanoic acids such as acetic acid are used, preference is given to using temperatures in the range from 50 to 100° C. The reaction time can be from a few minutes to several hours, for example from about 20 min to 5 h. Preferably, the compound IV to be reduced is initially charged in the reaction vessel, and with mixing the metal in question, preferably in finely divided form, in particular as powder, is then added to the reaction mixture. The addition is preferably carried out over a period of from 10 min to 2 h. Frequently, the resulting mixture is allowed to react at reaction temperature for a certain extra period of time, for example from 10 min to 4 h.

The reduction of IV to V is preferably carried out using iron powder in acetic acid. To this end, for example, the iron powder is initially charged in acetic acid and, at temperatures in the range from 50 to 100° C., preferably 65 to 75° C., the compound IV, preferably the dibromo compound IV (Hal=Br), is then added to the reaction vessel. The addition is preferably carried out over a period of from 20 to 60 min, with mixing of the components, for example with stirring. After the addition has ended, the mixture is allowed to react for an extra 0.5 to 2 h, preferably about 1 h, at reaction temperature, preferably at 65 to 75° C. However, it is also possible to add the iron powder with stirring to the mixture of the compound IV in glacial acetic acid and to terminate the reaction as above. The amount of iron powder is preferably 2 to 5 mol, in particular 2.5 to 4 mol, per mole of nitrophenoxypropionic acid derivative IV. The reduction can be carried out continuously or batchwise.

The 2-(3-nitro(thio)phenoxy)-2,3-dihalopropionic acid(s) (esters) IV are advantageously prepared from the corresponding 2-(3-nitro(thio)phenoxy)propionic acid esters of the formula IX by halogenation with a halogenating agent, such as elemental chlorine or bromine, preferably elemental bromine. In the formula IX, $R^1$, $R^2$, $R^{3'}$, Hal and Z are as defined above.

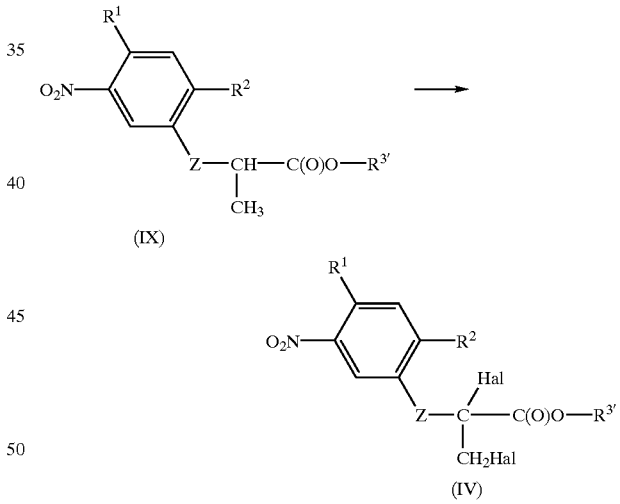

The reaction is generally carried out in the presence of a free-radical initiator, for example di-tert-butyl peroxide, benzoyl peroxide or azoisobutyronitrile.

The halogenation of IX is usually carried out in an inert solvent, for example in chlorinated hydrocarbons, such as chlorobenzene, 1,2-, 1,3-, 1,4-dichlorobenzene, 1,2,4-trichlorobenzene, 1-chloronaphthalene, in nitriles, such as acetonitrile, propionitrile, butyronitrile, in carboxylic acids, such as acetic acid or propionic acid, furthermore in water or in mixtures of the abovementioned solvents.

The amount of halogenating agents is generally from 1.9 to 3.5 mol, preferably from 2.0 to 3.1 mol, particularly preferably from 2.2 to 3.0 mol, per mole of nitrophenoxypropionic acid derivative IX. The reaction is generally carried out at temperatures in the range from 50 to 200° C., in particular 100 to 150° C. The reaction time is generally from 0.5 to 30 h and in particular from 1 to 20 h. The reaction can be carried out continuously or batchwise, under atmospheric pressure or under superatmospheric pressure.

In a preferred embodiment of the halogenation of IX to give IV, the nitro(thio)phenoxypropionic acid ester of the formula IX is initially charged, neat or in one of the abovementioned inert solvents, a free-radical initiator is, if desired, added and, with mixing, the halogenating agent is then added at the desired reaction temperature, for example at temperatures in the range from 100 to 140° C., over 1–10 h. Gaseous halogenating agents are preferably introduced as a gas, and liquid halogenating agents, such as elemental bromine, are added directly. The reaction mixture is then allowed to react for, preferably, a total of 10 to 30 h, in particular 15 to 25 h, at 140 to 150° C.

The 2-(3-nitro(thio)phenoxy)propionic acid derivatives of the formula IX can be prepared by reacting 3-nitrophenols of the formula VI (Z=O) or 3-nitrothiophenols of the formula VI (Z=S) with propionic esters of the formula X which, in the 2-position, have a nucleophilically displaceable leaving group A, for example a halogen atom, such as chlorine or bromine. In the formulae VI, IX and X, the variables $R^1$, $R^2$, $R^{3'}$ and Z are as defined above. The group A in the propionic acid derivative of the formula X is the nucleophilically displaceable leaving group already mentioned. The reaction conditions for the conversion of VI and X into XI correspond to the conditions described in the literature, for example in DE-A 28 01 429, for similar reactions.

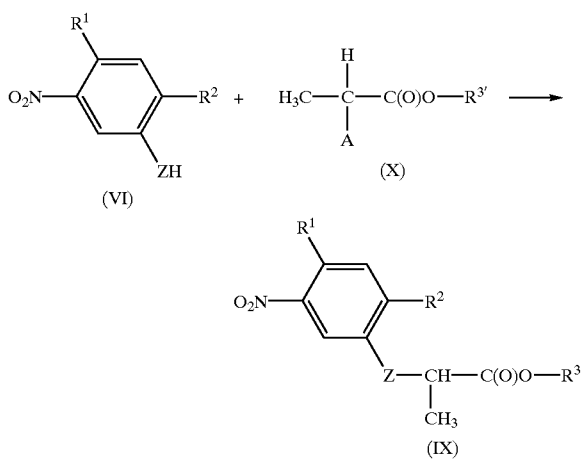

The reaction of VI with X to give IX is usually carried out in an inert organic solvent, suitable solvents being, in particular, aprotic solvents, for example aliphatic and cyclic ethers, such as 1,2-dimethoxyethane, tetrahydrofuran and dioxane, aliphatic ketones, such as acetone, amides, such as dimethylformamide, sulfoxides, such as dimethyl sulfoxide, ureas, such as tetramethylurea and 1,3-dimethyltetrahydro-2(1H)-pyrimidinone, carboxylic esters, such as ethyl acetate, or halogenated aliphatic or aromatic hydrocarbons, such as dichloromethane and chlorobenzene.

The reaction of VI with X to give IX is preferably carried out in the presence of an auxiliary base. Suitable bases are both inorganic bases, for example alkali metal carbonates, such as sodium carbonate and potassium carbonate, alkali metal bicarbonates, such as sodium bicarbonate and potassium bicarbonate, or alkali metal hydrides, such as sodium hydride and potassium hydride, and organic bases, for example amines, such as triethylamine, pyridine and N,N-diethylaniline, or alkali metal alkoxides, such as sodium methoxide, sodium ethoxide and potassium tert-butoxide.

The base is generally employed in an amount of from 0.5 to 2 mol, preferably from 0.9 to 1.1 mol, based on 1 mol of nitrophenol VI. The propionic acid derivative X is generally likewise employed in an amount of from 0.5 to 2 mol, preferably from 0.9 to 1.1 mol, based on 1 mol of nitrophenol VI.

In general, a reaction temperature of from 0° C. to the boiling point of the reaction mixture, in particular from 0 to 60° C., is recommended.

The reaction mixtures are generally worked up by methods known per se, for example by diluting the reaction solution with water, followed by isolation of the product by filtration, crystallization or solvent extraction, or by removal of the solvent, partitioning of the residue in a mixture of water and a suitable organic solvent and work-up of the organic phase to afford the product. The work-up methods described here can also be used for the other conversions described here. The selection of a suitable work-up method is known to the person skilled in the art.

The resulting amino(thio)phenoxyacrylic acid derivatives of the formula IIIa or V can be converted by methods known per se into the compounds of the formula I.

The synthesis of heterocyclic groups of the formulae II-1 to II-19 in phenyl-substituted heterocycles starting from aniline derivatives has been described frequently in the literature, and the synthesis can be carried out directly from anilines or from isocyanates, isothiocyanates or phenylhydrazines. In the present case, the phenyl isocyanates IIIc ($R^y$=N=C=O), the phenyl isothiocyanates IIId ($R^y$=N=C=S) and the phenylhydrazines ($R^y$=NH—NH$_2$) can likewise be prepared starting with the anilines IIIa ($R^y$=NH$_2$), using methods known per se (see, for example, R. Richter, H. Ulrich, "Synthesis and preparative application of isocyanates" in Patai: The Chemistry of Cyanates and their thioderivatives, pp. 619–818, New York, Wiley 1997; R. G. Guy, "synthesis and preparative application of thiocyanates", ibid, pp. 819–886; Houben-Weyl, Methoden der Organischen Chemie, IVth edition, Volume X/2, pp. 177–347).

Compounds of the formula I having a heterocyclic radical of the formula II-5 can be synthesized, for example, by reacting the aniline IIIa with an appropriately substituted maleic anhydride. Thus, for example, compounds of the formula I in which Het is a 3,4,5,6-tetrahydroisoindoledione radical of the formula II-5 in which $R^4$ and $R^{4'}$ together with the attached cycle form a cyclohexene ring can be prepared by reacting an aniline of the formula IIIa with 3,4,5,6-tetrahydrophthalic anhydride under the reaction conditions given in EP-A 240 659.

1H-3-Phenyluracils of the formula I in which Het is a radical of the formula II-19 where X=O can be synthesized by reacting the phenyl isocyanates IIIc with appropriately substituted enamine esters, followed by ring closure under the reaction conditions described in WO 93/06090 (see, in particular, pages 56 and 57 and the Preparation Example pp. 98–99). The preparation of the enamine ester and enamine carboxylate precursors is likewise described in WO 93/06090 (see pages 74 to 86). WO 93/06090 is therefore expressly incorporated herein by way of reference.

Further preparation processes for phenyl-substituted heterocycles having groups Het of the formulae II-1 to II-19, which processes are suitable in an analogus manner for preparing the novel compounds I from the compounds of the formula III, are also described in DE-A 28 01 429, DE-A 197 08 928, WO 93/06090, WO 99/38861 and WO 99/52893. A list of suitable methods for preparing phenyl-substituted heterocycles having groups Het of the formulae II-1 to II-19 from anilines, phenyl iso(thio)cyanates and phenylhydrazines is also given in S. O. Duke, C. A. Rebeiz, Porphyric Pesticides, ACS Symp. Ser. 1994, 559, Washington D.C., 1994. The methods described therein are used in an analogous manner for preparing the novel compounds I from the compounds III. The abovementioned publications are therefore expressly incorporated herein by way of reference.

The compounds I and their agriculturally useful salts, both as isomer mixtures and in the form of the pure isomers, are suitable as herbicides. The herbicidal compositions comprising I effect very good control of vegetation on non-crop areas, especially at high rates of application. In crops such as wheat, rice, maize, soybeans and cotton, they act against broad-leaved weeds and grass weeds without damaging the crop plants substantially. This effect is observed especially at low rates of application.

Depending on the application method in question, the compounds I, or compositions comprising them, can additionally be employed in a further number of crop plants for eliminating undesirable plants. Suitable crops are, for example, the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I can also be used in crops which tolerate the action of herbicides due to breeding, including genetic engineering methods.

The herbicidal compositions or active ingredients can be applied pre- or post-emergence. If the active ingredients are less well tolerated by certain crop plants, it is possible to use application techniques in which the herbicidal compositions are sprayed, with the aid of the spraying equipment, in such a way that they come into as little contact as possible, if any, with the leaves of the sensitive crop plants while the active compounds reach the leaves of undesirable plants which grow underneath, or the bare soil surface (post-directed, lay-by).

The compounds I, or the herbicidal compositions comprising them, can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee thefinest possible distribution of the active compounds according to the invention.

Suitable inert additives are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substituted phenoxyacrylic acid derivatives, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignin-sulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active ingredients I in the ready-to-use products can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR spectrum).

The compounds I according to the invention can, for example, be formulated as follows:

I 20 parts by weight of the compound I in question are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II 20 parts by weight of the compound I in question are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III 20 parts by weight of the compound I in question are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV 20 parts by weight of the compound I in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V 3 parts by weight of the compound I in question are mixed with 97 parts by weight of finely divided kaolin. This gives a dust which comprises 3% by weight of the active ingredient.

VI 20 parts by weight of the compound I in question are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the compound I in question is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the compound I in question is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the spectrum of action and to achieve synergistic effects, the substituted phenoxyacrylic acid derivatives I may be mixed, and applied jointly, with a large number of representatives of other groups of herbicidal or growth-regulating active ingredients. Suitable examples of components in mixtures are 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexanediones, hetarylaryl ketones, benzylisoxazolidinones, meta-CF$_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxirans, phenols, aryloxy- and heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I, alone or in combination with other herbicides, in the form of a mixture with even further crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

Depending on the intended aim of control, the season, the target plants and the growth stage, the rates of application of active ingredient are from 0.001 to 3.0, preferably 0.01 to 1.0, kg of active substance (a.s.)/ha.

PREPARATION EXAMPLES

I Preparation of the Intermediates (Compounds 1 to 9)

I.1 Compound 1: Methyl 2-(2-chloro-4-fluoro-5-nitrophenoxy)propionate

At 22° C., 100 g (0.522 mol) of 2-chloro-4-fluoro-5-nitrophenol were added with stirring to a solution of 34.5 g (0.522 mol) of 85% strength potassium hydroxide in 500 ml of methanol, and the mixture was stirred for another 30 min. At 40° C., the reaction mixture was then concentrated under reduced pressure. The residue was dried at 50° C. in a vacuum cabinet overnight. The pulverulent residue was then, at 40° C., dissolved with stirring in 1 l of dimethylformamide (DMF), 70.7 g (0.574 mol) of methyl 2-chloropropionate were added dropwise at 50° C. over a period of 30 min and the mixture was stirred at 80° C. for another 2 h. The solvent was removed under reduced pressure, the residue was introduced into 700 ml of water and undissolved components were filtered off. The aqueous phase was extracted three times with in each case 300 ml of methyl tert-butyl ether. The combined organic extracts were washed with about 500 ml of saturated sodium chloride solution and dried over magnesium sulfate. Concentration gave 106 g (73.1% of theory) of the title compound as a colorless resin.

$^1$H-NMR (270 MHz, CDCl$_3$) δ [ppm]: Ar 7.52 (d/1), 7.4 (d/1); CH 4.82 (q/1); OCH$_3$ 3.8 (s/3); C—CH$_3$ 1.75 (d/3).

I.2 Compound 2: Methyl 2,3-dibromo-2-(2-chloro-4-fluoro-5-nitrophenoxy)propionate At 100° C., ⅘ of 182.17 g (1.14 mol) of bromine were added with stirring and over a period of 1 h to a mixture of 105.51 g (0.38 mol) of the Compound 1 and 3.12 g (19 mmol) of azoisobutyronitrile, and the mixture was heated at 140° C. for 12 h. The remaining bromine was then added over 30 min, and the mixture was stirred at 140° C. for a further 24 h. At 80° C./0.3 mbar, the reaction mixture was concentrated, giving 160.8 g (82.6% of theory at a purity of 85%) of the title compound as a resin.

¹H-NMR (270 MHz, CDCl₃) δ [ppm]: Ar 8.42 (d/1), 7.4 (d/1); CH₂ 4.35 (q/2); OCH₃ 3.95 (s/3).

I.3 Compound 3: Methyl 2-(5-amino-2-chloro-4-fluorophenoxy)acrylate

At 60° C., 135 g (0.314 mol) of the Compound 2 were dissolved in 400 ml of acetic acid and, with stirring and at 70° C., added over a period of 2.5 h to a suspension of 52.55 g (0.942 mol) of iron powder in 400 ml of acetic acid, the temperature increasing to 75–80° C. The mixture was stirred at 70° C. for 2 h and overnight at 22° C. About ⅔ of the solvent was then removed under reduced pressure, the residue was poured into ice-water, the mixture was extracted 4× with 750 ml of ethyl acetate and the combined organic extracts were washed 2× with saturated aqueous sodium bicarbonate solution and 1× with saturated sodium chloride solution. The solution was dried over magnesium sulfate and concentrated under reduced pressure, and the residue was chromatographed over silica gel using methylene chloride. Concentration of the first 4 fractions gave 64 g (74.5% of theory at a purity of 90%) and fractions 5 and 6 gave a further 7.8 g (purity: 60%) of the title compound as a yellow oil.

¹H-NMR (400 MHz, d₆-DMSO) δ [ppm]: Ar 7.27 (d/1), 6.52 (d/1); CH₂ 5.62 (d/1), 4.85 (d/1); OCH₃ 3.79 (s/1).

I.4 Compound 4: Methyl 2-(2-chloro-4-fluoro-5-isocyanatophenoxy)acrylate

At 15–20° C., 17.7 g (89.6 mmol) of diphosgene were added with stirring and over a period of 15 min to a mixture of 20 g (81.42 mmol) of the Compound 3 and 0.2 ml of pyridine in 200 ml of toluene. The mixture was initially stirred at 22° C. for 1 h and then, with heating at 110° C., up to a total of 10 h. Concentration gave 22.3 g of the title compound in a purity of 90%. 15.8 g (71.4% of theory) of the title compound were isolated as a yellowish oil by distillation at 130–140° C. (bath)/0.2–0.3 mbar.

IR (film) ν [cm⁻¹]: N=C=O 2259

I.5

The Compounds 5, 6, 7, 8 and 9 listed in Table 1 were obtained in an analogous manner, starting from 4-chloro-2-fluoro-5-nitrophenol and ethyl 2-chloropropionate.

TABLE 1

| Compound | Formula | Yield (%) | HPLC * [min] |
|---|---|---|---|
| 5 | (F, Cl, O₂N-Ar-O-CH(CH₃)-CO₂C₂H₅) | 80.3 | 6.62 |
| 6 | (F, Cl, H₂N-Ar-O-C(CH₂Br)(Br)-CO₂C₂H₅) | 80 | 10.44 |
| 7 | (F, Cl, H₂N-Ar-O-C(=CH₂)-CO₂C₂H₅) | 55.4 | 5.3 |
| 8 | (F, Cl, O=C=N-Ar-O-C(=CH₂)-CO₂C₂H₅) | 77.2 | b.p. 138–145° C./0.2 mbar (bath) |

TABLE 1-continued

| Compound | Formula | Yield (%) | HPLC * [min] |
|---|---|---|---|
| 9 | (structure: S=C=N on fluoro/chloro-substituted phenyl with O-C(=CH$_2$)-CO$_2$C$_2$H$_5$) | 95 | m.p. 62–63° C. |

* Retention in min (Li-Chrospher column 25 × 0.4 cm, RP-18, CH$_3$CN:H$_2$O = 60:40 to 80:20)

II Preparation of the Compounds of the Formula I According to the Invention (Examples 1 to 13)

Example 1

3-(4-chloro-2-fluoro-5-(1-methoxycarbonyl-1-vinyloxy)phenyl)-6-trifluoromethyl-2,4-(1H,3H) pyrimidinedione With stirring and under an atmosphere of nitrogen, 0.78 g (30.92 mmol) of 95% strength sodium hydride were added, at 15° C., to 170 ml of dimethylformamide; 5.0 g (29.45 mmol) of methyl 3-amino-4,4,4-trifluorocrotonate in 5 ml of DMF were added over a period of 5 min at 0–5° C., and the mixture was allowed to react at 0–5° C. for 1 h. Over a period of 10 min, a solution of 8.0 g (29.45 mmol) of the Compound 4 in 35 ml of tetrahydrofuran was added with stirring, at from −30 to −35° C., to the resulting solution. The mixture was kept at −30° C. for another 30 min and then allowed, with stirring, to warm from −30 to 15° C. over a period of 1.5 h. The reaction mixture was poured into ice-water, the pH was adjusted to pH 6.5 using 2 N hydrochloric acid and the mixture was extracted 5× with methyl tert-butyl ether. The organic phase was washed with water, dried and concentrated, giving 8.3 g of the crude title compound. The residue was dissolved in methylene chloride and chromatographed over silica gel, and 6.0 g (49.8% of theory) of the title compound were isolated as colorless crystals of m.p. 171–173° C.

Example 2

3-(4–Chloro-2-fluoro-5-(1-methoxycarbonyl-1-vinyloxy)phenyl)-1-methyl-6-trifluoromethyl-2,4-(1H, 3H)pyrimidinedione At 22° C. and with stirring, 0.57 g (4.037 mmol) of methyl iodide was added to a mixture of 1.5 g (3.67 mmol) of the compound from Example 1 and 0.56 g (4.037 mmol) of finely powdered potassium carbonate in 20 ml of DMF, and the mixture was stirred at 22° C. overnight. The reaction mixture was stirred into a mixture of 5 ml of conc. hydrochloric acid and 1.5 l of ice-water, and the pH was adjusted with saturated sodium bicarbonate solution to pH 6.5. The mixture was extracted 3× with methyl tert-butyl ether, and the extract was washed with water, dried and concentrated under reduced pressure. This gave 1.3 g (83.8% of theory) of the title compound as a colorless resin.

$^1$H-NMR (400 MHz, CDCl$_3$) δ [ppm]: CH 6.35 (s/1); CH$_2$ 5.76 (d/1), 4.88 (d/1); OCH$_3$ 3.84 (s/3); N—CH$_3$ 3.55 (s/3)

Example 3

3-(4-Chloro-2-fluoro-5-(1-methoxycarbonyl-1-vinyloxy)phenyl)-1-amino-6-trifluoromethyl-2,4-(1H, 3H)pyrimidinedione Reaction of 1.5 g (3.67 mmol) of the compound from Example 1, 0.1 g (4.037 mmol) of sodium hydride and 0.73 g (3.67 mmol) of 2,4-dinitrophenoxyamine in 55 ml of DMF by the method described in Example 2 gave 0.83 g (53.4% of theory) of the title compound as colorless crystals of m.p. 66° C.

Example 4

N-(4-chloro-2-fluoro-5-(1-ethoxycarbonyl-1-vinyloxy)phenyl)-4,5,6,7-tetrahydrophthalimide 0.76 g (5.0 mmol) of 3,4,5,6-tetrahydrophthalic anhydride and 1.3 g (5.0 mmol) of the Compound 7 were dissolved in 50 ml of propionic acid and the mixture was stirred at 115° C. for 11 h. The reaction mixture was stirred into 700 ml of water and extracted 3× with methylene chloride, and the extract was washed 2× with saturated aqueous sodium bicarbonate solution. Drying, chromatography over silica gel (dichloromethane) and concentration gave 1.16 g (58.8% of theory) of the title compound as a colorless resin; HPLC 7.92, IR (film) C=O 1720 cm$^{-1}$.

Example 5

Methyl 2-[2-chloro-4-fluoro-5-(4-thioxo-N,N-dimethyltriazine-2,6-dion-1-yl)phenoxy]acrylate A solution of 0.20 g (1.84 mmol) of N,N'-dimethylthiourea in 5 ml of toluene was mixed successively at room temperature with 0.06 ml of triethylamine, a solution of 0.5 g (1.84 mmol) of methyl 2-(2-chloro-4-fluoro-5-isocyanatophenoxy)acrylate in 5 ml of toluene and 0.60 g (3.68 mmol) of carbodiimidazole. The mixture was then heated at 80° C. for 6 h. The reaction mixture was then washed three times with water and concentrated under reduced pressure. The residue (0.83 g) was chromatographed over silica gel (cyclohexane/ethyl acetate 20:1), giving 140 mg of the title compound as a viscous oil. The yield was 19% ($^1$H-NMR data: see Table 2).

In addition to the Examples 1 to 5 described above, Table 2 below lists further substituted phenoxyacrylates of the formula I which were prepared in a similar manner (Examples 6 to 10).

TABLE 2
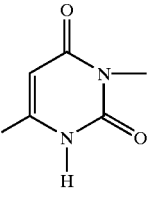
| No. | Het | R¹ | R² | R³ | m.p., IR [cm⁻¹], HPLC* ¹H—NMR |
|---|---|---|---|---|---|
| 1 | 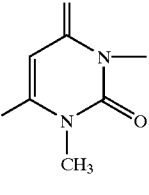 | F | Cl | $CH_3$ | 171–173° C. |
| 2 | 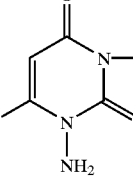 | F | Cl | $CH_3$ | Resin, νC=O 1736, 1690; 5.79 min |
| 3 | 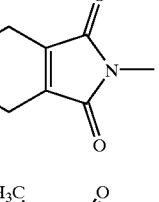 | F | Cl | $CH_3$ | 66° C. |
| 4 | 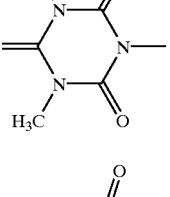 | F | Cl | $CH_3$ | 99–102° C. |
| 5 | 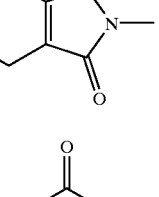 | F | Cl | $CH_3$ | δ(ppm): 3.75(s, 6H), 3.85(s, 3.85), 4.9(d, 1H), 5.75(d, 1H), 7.05(d, 1H), 7.4(d, 1H)133–136° C. |
| 6 | 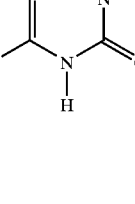 | F | Cl | $C_2H_5$ | Resin, νC=O 1720; 7.92 min |
| 7 |  | F | Cl | $C_2H_5$ | Resin, νC=O 1741, 1691; 1.34 min |

TABLE 2-continued

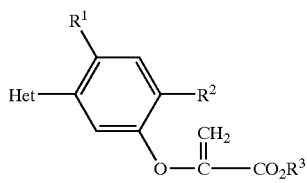

| No. | Het | R¹ | R² | R³ | m.p., IR [cm⁻¹], HPLC* ¹H—NMR |
|---|---|---|---|---|---|
| 8 | F₃C–[pyrimidine-2,4-dione, N-CH₃, N-CH₃] | F | Cl | C₂H₅ | Resin, νC=O 1735, 1689; 6.15 min |
| 9 | F₃C–[pyrimidine-2,4-dione, N-CH₃, N-NH₂] | F | Cl | C₂H₅ | Resin, νC=O 1737, 1687; 5.4 min |
| 10 | F₃C–[pyrimidine-2,4-dione, N-CH₃, N⁻Na⁺] | F | Cl | CH₃ | >260° C. (obtainable by reacting Example 1 with 1 eq. of sodium methoxide in methanol (30% strength by weight solution) at 22° C. and concentration under reduced pressure) |
| 11 | F₃C–[pyrimidine-2,4-dione, N-CH₃, N-CH₃] | F | Cl | CH₂—C≡CH | Harz, ν(C=O) 1735, 1687; 5.41 Min. |
| 12 | F₃C–[pyrimidine-4-one-2-thione, N-CH₃, N-CH₃] | F | Cl | CH₃ |  |
| 13 | F₃C–[pyrimidine-2,4-dione, N-CH₃, N-CH₃] | F | Cl | H | 74–76° C. |

*HPLC see Table 1

Use Examples

The herbicidal action of the substituted phenoxyacrylic acid derivatives of the formula I was demonstrated by greenhouse experiments:

The culture containers used were plastic pots containing loamy sand with approximately 3.0% of humus as substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants, unless this was adversely affected by the active ingredients.

For the post-emergence treatment, the test plants were first grown to a height of 3 to 15 cm, depending on the plant habit, and then treated with the active ingredients which had been suspended or emulsified in water. For this purpose, the test plants were either sown directly and grown in the same containers, or they were first grown separately as seedlings and transplanted into the test containers a few days prior to treatment. The application rate for the post-emergence treatment was 1.95 and 3.9 g of a.s./ha.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments were of the following species:

| Bayer code | Common name |
| --- | --- |
| TRZAW | winter wheat |
| ABUTH | velvet leaf |
| AMARE | redroot pigweed |
| IPOSS | morning glory |
| SOLNI | black nightshade |

The Compound I according to the invention from Example 2 and a compound analogous to Example 1 of EP-A 255 047 (Comparative Example A) were examined.

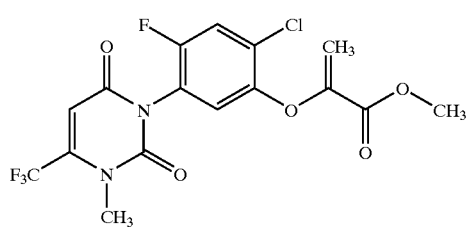

(Example 2)

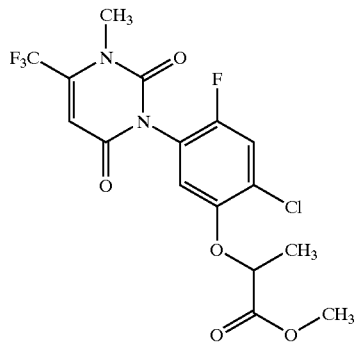

(Comparative Example A)

At application rates of 3.9 and 1.95 g/ha of a.s., the compound from Example 2 was tolerated considerably better by the crop wheat (TRZAW) than the compound of Comparative Example A and had at least as good a herbicidal effect on dicotyledonous harmful plants.

We claim:

1. A phenoxy- or thiophenoxyacrylic acid compound of the formula

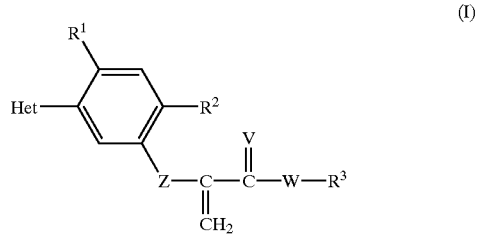

(I)

in which

Z, V and W independently of one another are oxygen or sulfur, $R^1$ is hydrogen or halogen and $R^2$ is halogen, cyano, $C_1$–$C_6$-alkyl, $C_1$–$C_6$-haloalkyl, $C_1$–$C_6$-alkoxy or $C_1$–$C_6$-haloalkoxy;

$R^3$ is hydrogen, $C_1$–$C_6$-alkyl, $C_2$–$C_6$-alkenyl, $C_3$–$C_6$-alkynyl, $C_1$–$C_6$-alkylamino-$C_1$–$C_6$-alkyl, ($C_1$–$C_6$-alkoxy)carbonyl-$C_1$–$C_6$-alkyl, $C_3$–$C_8$-cycloalkyl, 2,3-dihydrofuryl, 2,5-dihydrofuryl, tetrahydrofuryl, where each of the ten last mentioned groups may carry one, two or three substituents selected from the group consisting of:

halogen, nitro, cyano, hydroxyl, $C_3$–$C_6$-cycloalkyl, $C_1$–$C_6$-alkoxy, $C_1$–$C_6$-alkoxy-$C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkylcarbonyl, $C_1$–$C_6$-alkylcarbonyloxy, ($C_2$–$C_6$-alkenyl)carbonyloxy, ($C_2$–$C_6$-alkynyl)carbonyloxy, $C_1$–$C_6$-alkylthio, $C_1$–$C_6$-alkylsulfinyl, $C_1$–$C_6$-alkylsulfonyl, $C_1$–$C_6$-alkylideneiminooxy, =N—$OR^8$, —O—($C_nH_{2n-1}$)=N—$OR^8$ where n=1, 2, 3, 4, 5 or 6, phenyl, benzyloxy, phenoxy or phenylsulfonyl, where the three last mentioned groups may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy or $C_1$–$C_6$-alkoxycarbonyl;

is ($C_3$–$C_6$-alkenyloxy)carbonyl-$C_1$–$C_6$-alkyl, ($C_3$–$C_6$-alkynyloxy)carbonyl-$C_1$–$C_6$-alkyl, furyl or phenyl, where furyl and phenyl independently of one another may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy or $C_1$–$C_6$-alkoxycarbonyl;

Het is an unsaturated five- or six-membered heterocyclic radical which is attached to the phenyl ring of I via a nitrogen atom and which is selected from among radicals of the formulae II-1 to II-19:

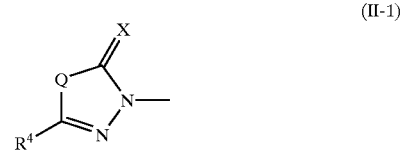

(II-1)

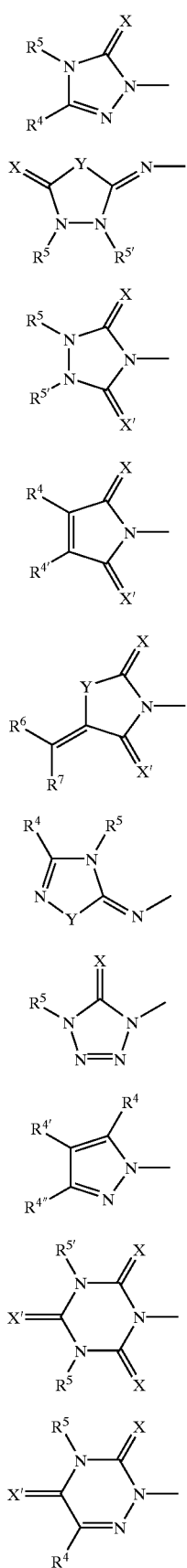
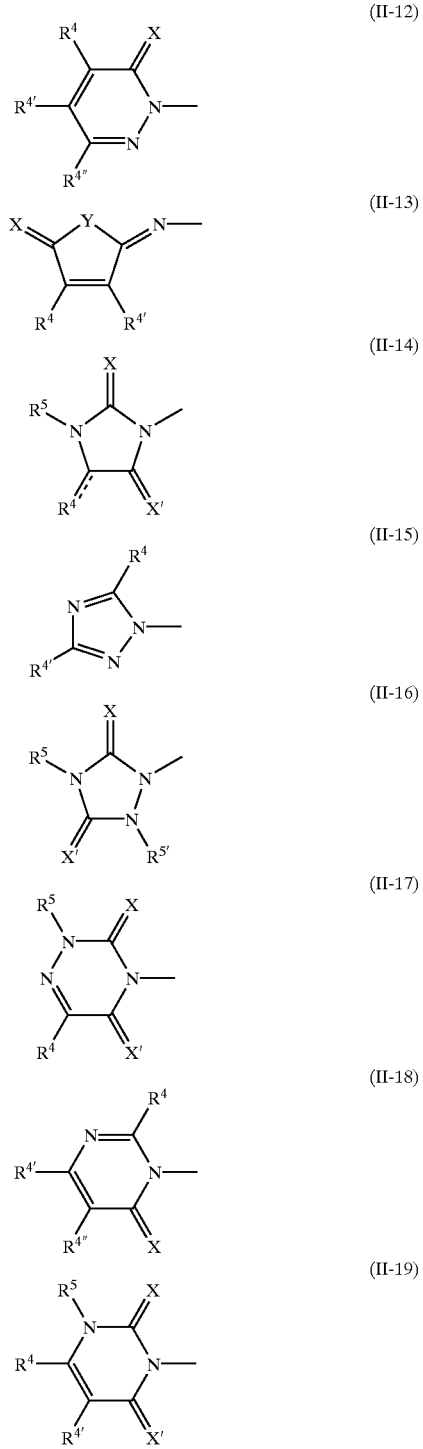

in which ==== denotes a single bond or a double bond, $R^4$, $R^{4'}$ and $R^{4''}$ independently of one another are hydrogen, amino, $C_1$–$C_4$-alkylamino, di-$C_1$–$C_4$-alkylamino, saturated 5- or 6-membered N-bonded nitrogen heterocyclyl, $C_3$–$C_6$-cycloalkylamino, halogen, cyano, carboxyl, $C_1$–$C_6$-alkyl, $C_1$–$C_6$-haloalkyl, $C_3$–$C_6$-alkenyl, $C_3$–$C_6$-alkynyl, $C_1$–$C_6$-alkoxy, $C_1$–$C_6$-haloalkoxy, $C_1$–$C_6$-haloalkylthio, $C_1$–$C_6$-alkoxycarbonyl, $C_3$–$C_6$-alkenyloxy, $C_3$–$C_6$-alkynyloxy, $C_1$–$C_6$-alkylthio, $C_1$–$C_6$-alkylsulfinyl, $C_1$–$C_6$-alkylsulfonyl, $C_3$–$C_8$-cycloalkyl or $C_3$–$C_8$-cycloalkyl-$C_1$–$C_6$-alkyl, and $R^4$ in the formula II-14 is also a corresponding imino radical or alkylidene radical if ==== denotes a double bond;

$R^5$ and $R^{5'}$ independently of one another are hydrogen, amino, hydroxyl, cyano, $C_1$–$C_6$-alkyl, $C_1$–$C_6$-haloalkyl, $C_3$–$C_6$-alkenyl, $C_3$–$C_6$-alkynyl, $C_1$–$C_6$-alkoxycarbonyl, $C_3$–$C_8$-cycloalkyl, $C_3$–$C_8$-cycloalkyl-$C_1$–$C_6$-alkyl, phenyl or phenyl-$C_1$–$C_6$-alkyl; and/or in each case two of the radicals $R^4$, $R^{4'}$, $R^{4''}$, $R^5$ and $R^{5'}$ together with the ring atoms of Het to which they are attached form a 4-, 5-, 6- or 7-membered ring which may be saturated or unsaturated, which may contain one or two nitrogen, oxygen and/or sulfur atoms as ring members and/or which may be substituted by one, two or three radicals selected from the group consisting of $C_1$–$C_4$-alkyl and halogen;

$R^6$ and $R^7$ independently of one another are hydrogen, $C_1$–$C_6$-alkyl, $C_1$–$C_6$-haloalkyl or $C_3$–$C_6$-cycloalkyl, or together with the C atom to which they are attached form a 4-, 5-, 6- or 7-membered ring which may be saturated or unsaturated, which may contain one or two oxygen and/or sulfur atoms as ring members and/or which may be substituted by one, two or three substituents selected from the group consisting of $C_1$–$C_4$-alkyl and halogen;

$R^8$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkyhyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkyl)carbonyl-$C_1$–$C_6$-alkyl, ($C_1$–$C_6$-alkoxy)carbonyl-$C_1$–$C_6$-alkyl or ($C_1$–$C_6$-alkoxy)carbonyl-$C_2$–$C_6$-alkenyl;

Q in the formula II-1 is O or S,

X and X' independently of one another are O or S, and Y is O, S or a group N—$R^9$ in which $R^9$ is hydrogen, $C_1$–$C_6$-alkyl, $C_1$–$C_6$-haloalkyl or $C_3$–$C_8$-cycloalkyl;

and the agriculturally useful salts of the compound of the formula I.

2. A compound as claimed in claim 1 in which Het is a cycle of the formula II-3, II-7 or II-13 which is attached via an exocyclic imine nitrogen.

3. A compound as claimed in claim 1 in which Het is a nitrogen heterocycle of the formula II-4, II-5, II-6, II-10, II-14, II-17 or II-19 which is attached via an imide nitrogen.

4. A compound as claimed in claim 3 in which Het is a nitrogen heterocycle of the formula II-5, II-10, or II-19.

5. A compound as claimed in claim 3 in which X and X' are oxygen.

6. A compound as claimed in claim 1 in which Het is a nitrogen heterocycle which has at least one carbonyl or thiocarbonyl function and at least one endocyclic hydrazone structure and which is selected from among the radicals of the formulae II-1, II-2, II-11 and II-12.

7. A compound as claimed in claim 1 in which $R^1$ is hydrogen, fluorine or chlorine and $R^2$ is halogen or cyano.

8. A compound as claimed in claim 1 in which $R^3$ is hydrogen, $C_1$–$C_6$-alkyl, $C_1$–$C_6$-haloalkyl, nitro-$C_1$–$C_6$-alkyl, cyano-$C_1$–$C_6$-alkyl, hydroxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylideneiminooxy-$C_1$–$C_6$-alkyl, $C_1$–$C_6$-alkylcarbonyl-$C_1$–$C_6$-alkyl, ($C_1$–$C_6$-alkyl)carbonyloxy-$C_1$–$C_6$-alkyl, $C_3$–$C_8$-cycloalkyl, $C_3$–$C_8$-cycloalkyl-$C_1$–$C_6$-alkyl, $C_3$–$C_6$-cycloalkoxy-$C_1$–$C_6$-alkyl, $C_2$–$C_6$-alkenyl, $C_3$–$C_6$-alkynyl, $C_2$–$C_6$-haloalkenyl, $C_3$–$C_6$-haloalkynyl, $C_3$–$C_6$-alkenyloxy-$C_1$–$C_6$-alkyl, $C_3$–$C_6$-alkynyloxy-$C_1$–$C_6$-alkyl, ($C_2$–$C_6$-alkenyl)carbonyloxy-$C_1$–$C_6$-alkyl, ($C_2$–$C_6$-alkynyl)carbonyloxy-$C_1$–$C_6$-alkyl, ($C_3$–$C_6$-alkenyloxy)carbonyl-$C_1$–$C_6$-alkyl, ($C_3$–$C_6$-alkynyloxy)carbonyl-$C_1$–$C_6$-alkyl, $C_1$–$C_6$-alkoxy-$C_1$–$C_6$-alkyl, $C_1$–$C_6$-alkoxyimino-$C_1$–$C_6$-alkyl, $C_1$–$C_6$-alkoxyimino-$C_1$–$C_6$-alkoxy-$C_1$–$C_6$-alkyl, N—($C_1$–$C_6$-alkoxy-$C_1$–$C_6$-alkyl)amino-$C_1$–$C_6$-alkyl, ($C_1$–$C_6$-alkoxy)carbonyl-$C_1$–$C_6$-alkyl, 2,3-dihydrofuryl, 2,5-dihydrofuryl, tetrahydrofuryl, furyl, phenyl, phenyl-$C_1$–$C_6$-alkyl, benzyloxy-$C_1$–$C_6$-alkyl, phenoxy-$C_1$–$C_6$-alkyl or phenylsulfonyl-$C_1$–$C_6$-alkyl, where furyl and the phenyl rings of the 5 last mentioned groups may carry one, two or three substituents selected from the group consisting of halogen, nitro, cyano, $C_1$–$C_6$-alkyl, $C_1$–$C_6$-haloalkyl, $C_1$–$C_6$-alkoxy, $C_1$–$C_6$-haloalkoxy and $C_1$–$C_6$-alkoxycarbonyl.

9. A composition, comprising at least one substituted phenoxy- or thiophenoxyacrylic acid compound of the formula I or an agriculturally useful salt of I as claimed in claim 1 and customary auxiliaries.

10. A method for controlling undesirable vegetation, which comprises allowing a herbicidally active amount of at least one compound of the formula I or an agriculturally useful salt of I as claimed in claim 1 to act on plants, their habitat and/or on seeds.

\* \* \* \* \*

UNITED STATES PATENT AND TRADEMARK OFFICE
CERTIFICATE OF CORRECTION

PATENT NO. : 6,528,455 B1
DATED : March 4, 2003
INVENTOR(S) : Hamprecht et al.

It is certified that error appears in the above-identified patent and that said Letters Patent is hereby corrected as shown below:

Title page, Item [54] and Column 1, line 1,
"PHENOXY-AND" should be -- PHENOXY AND --.

Column 57,
Line 29, "$C_3$-$C_6$-alkyhyl" should be -- $C_3$-$C_6$-alkynyl --.

Signed and Sealed this

Ninth Day of September, 2003

JAMES E. ROGAN
*Director of the United States Patent and Trademark Office*